US008613748B2

(12) United States Patent
Velusamy et al.

(10) Patent No.: US 8,613,748 B2
(45) Date of Patent: Dec. 24, 2013

(54) APPARATUS AND METHOD FOR STABILIZING A NEEDLE

(75) Inventors: Gnanasekar Velusamy, Tamilnadu (IN); Alan Bachman, Milford, CT (US)

(73) Assignee: Perfint Healthcare Private Limited (IN)

( * ) Notice: Subject to any disclaimer, the term of this patent is extended or adjusted under 35 U.S.C. 154(b) by 23 days.

(21) Appl. No.: 13/435,963

(22) Filed: Mar. 30, 2012

(65) Prior Publication Data

US 2012/0184956 A1    Jul. 19, 2012

Related U.S. Application Data

(63) Continuation of application No. 13/292,186, filed on Nov. 9, 2011.

(30) Foreign Application Priority Data

Nov. 10, 2010    (IN) .......................... 3363/CHE/2010

(51) Int. Cl.
*A61B 19/00*    (2006.01)

(52) U.S. Cl.
USPC ........................................................ 606/130

(58) Field of Classification Search
USPC ........................................................ 606/130
See application file for complete search history.

(56) References Cited

U.S. PATENT DOCUMENTS

| | | | |
|---|---|---|---|
| 4,583,538 A | | 4/1986 | Onik et al. |
| 4,883,053 A | | 11/1989 | Simon |
| 5,078,140 A | | 1/1992 | Kwoh |
| 5,201,742 A | | 4/1993 | Hasson |
| 5,263,939 A | * | 11/1993 | Wortrich ........................ 604/174 |
| 5,269,305 A | * | 12/1993 | Corol ............................... 600/429 |
| 5,371,778 A | | 12/1994 | Yanof et al. |
| 5,590,655 A | | 1/1997 | Hussman |

(Continued)

FOREIGN PATENT DOCUMENTS

| | | |
|---|---|---|
| EP | 1103223 A2 | 5/2001 |
| EP | 1524626 A2 | 4/2005 |

(Continued)

OTHER PUBLICATIONS

International Search Report and Written Opinion for PCT/IN08/00507, mailed on Mar. 23, 2009; 7 pages.

(Continued)

*Primary Examiner* — Gary Jackson
*Assistant Examiner* — Eric Blatt
(74) *Attorney, Agent, or Firm* — Cooley LLP

(57) ABSTRACT

Apparatus and methods for use in an image-guided interventional procedure are described herein. In one embodiment, an apparatus includes a base configured to be releasably coupled to a patient's skin. A support portion extends from the base at an angle transverse to a longitudinal axis defined by the base. The support portion has a first end portion and a second end portion. The first end portion is disposed adjacent the base. A holder portion extends from the second end portion of the support portion. The holder portion defines an opening and is configured to be moved between a first configuration in which the opening defined by the holder portion has a first size and is configured to movably receive an interventional tool therethrough, and a second configuration in which the opening defined by the holder portion has a second size different than the first size.

21 Claims, 25 Drawing Sheets

(56) References Cited

U.S. PATENT DOCUMENTS

| | | |
|---|---|---|
| 5,628,327 A | 5/1997 | Unger et al. |
| 5,734,384 A | 3/1998 | Yanof et al. |
| 5,769,086 A | 6/1998 | Ritchart et al. |
| 5,814,038 A | 9/1998 | Jensen et al. |
| 5,823,993 A | 10/1998 | Lemelson |
| 5,834,759 A | 11/1998 | Glossop |
| 5,957,933 A | 9/1999 | Yanof et al. |
| 6,021,342 A | 2/2000 | Brabrand |
| 6,035,228 A | 3/2000 | Yanof et al. |
| 6,052,611 A | 4/2000 | Yanof et al. |
| 6,064,904 A | 5/2000 | Yanof et al. |
| 6,097,994 A | 8/2000 | Navab et al. |
| 6,110,112 A | 8/2000 | Heywang-Koebrunner |
| 6,139,544 A | 10/2000 | Mikus et al. |
| 6,149,592 A | 11/2000 | Yanof et al. |
| 6,167,296 A | 12/2000 | Shahidi |
| 6,176,835 B1 | 1/2001 | Pachal |
| 6,185,445 B1 | 2/2001 | Knüttel |
| 6,203,543 B1 | 3/2001 | Glossop |
| 6,216,029 B1 | 4/2001 | Paltieli |
| 6,245,028 B1 | 6/2001 | Furst et al. |
| 6,246,898 B1 | 6/2001 | Vesely et al. |
| 6,249,713 B1 | 6/2001 | Geiger et al. |
| 6,317,616 B1 | 11/2001 | Glossop |
| 6,334,067 B1 | 12/2001 | Brabrand |
| 6,366,796 B1 | 4/2002 | Yanof et al. |
| 6,442,417 B1 | 8/2002 | Shahidi et al. |
| 6,443,960 B1 | 9/2002 | Brabrand et al. |
| 6,468,226 B1 | 10/2002 | McIntyre, IV |
| D466,609 S | 12/2002 | Glossop |
| 6,505,065 B1 | 1/2003 | Yanof et al. |
| 6,529,758 B2 | 3/2003 | Shahidi |
| 6,546,279 B1 | 4/2003 | Bova et al. |
| 6,575,969 B1 | 6/2003 | Rittman, III et al. |
| 6,591,130 B2 | 7/2003 | Shahidi |
| 6,665,554 B1 | 12/2003 | Charles et al. |
| 6,674,833 B2 | 1/2004 | Shahidi et al. |
| 6,687,529 B2 | 2/2004 | Van Vaals |
| 6,694,164 B2 | 2/2004 | Glossop |
| 6,695,786 B2 | 2/2004 | Wang et al. |
| 6,778,850 B1 | 8/2004 | Adler et al. |
| 6,782,287 B2 | 8/2004 | Grzeszczuk et al. |
| 6,785,571 B2 | 8/2004 | Glossop |
| 6,785,572 B2 | 8/2004 | Yanof et al. |
| 6,827,712 B2 | 12/2004 | Tovey et al. |
| 6,850,794 B2 | 2/2005 | Shahidi |
| 6,853,856 B2 | 2/2005 | Yanof et al. |
| 6,889,073 B2 | 5/2005 | Lampman et al. |
| 7,008,373 B2 | 3/2006 | Stoianovici et al. |
| 7,182,083 B2 | 2/2007 | Yanof et al. |
| 7,192,430 B2 | 3/2007 | Truckai et al. |
| 7,225,012 B1 | 5/2007 | Susil et al. |
| 7,245,958 B1 | 7/2007 | Navab et al. |
| 7,322,990 B1 | 1/2008 | Mark et al. |
| 7,333,644 B2 | 2/2008 | Jerebko et al. |
| 7,379,769 B2 | 5/2008 | Piron et al. |
| 7,398,116 B2 | 7/2008 | Edwards |
| 7,440,793 B2 | 10/2008 | Chauhan et al. |
| 7,466,303 B2 | 12/2008 | Yi et al. |
| 7,608,083 B2 | 10/2009 | Lee et al. |
| 7,660,623 B2 | 2/2010 | Hunter et al. |
| 7,722,565 B2 | 5/2010 | Wood et al. |
| 7,742,801 B2 | 6/2010 | Neubauer et al. |
| 7,751,868 B2 | 7/2010 | Glossop |
| 7,752,920 B2 | 7/2010 | Blumenkranz et al. |
| 7,801,583 B2 | 9/2010 | Brabrand |
| 7,805,269 B2 | 9/2010 | Glossop |
| 7,822,466 B2 | 10/2010 | Stoianovici et al. |
| 7,824,417 B2 | 11/2010 | Magnusson et al. |
| 7,840,251 B2 | 11/2010 | Glossop |
| 7,840,254 B2 | 11/2010 | Glossop |
| 7,853,307 B2 | 12/2010 | Edwards |
| 7,871,406 B2 | 1/2011 | Nields et al. |
| 7,920,909 B2 | 4/2011 | Lyon et al. |
| 7,962,193 B2 | 6/2011 | Edwards et al. |
| 8,041,412 B2 | 10/2011 | Glossop et al. |
| 8,150,495 B2 | 4/2012 | Edwards et al. |
| 8,155,416 B2 | 4/2012 | Nields et al. |
| 2001/0025183 A1 | 9/2001 | Shahidi |
| 2001/0037064 A1 | 11/2001 | Shahidi |
| 2002/0143317 A1 | 10/2002 | Glossop |
| 2002/0156376 A1 | 10/2002 | Wang et al. |
| 2003/0018251 A1 | 1/2003 | Solomon |
| 2003/0032878 A1 | 2/2003 | Shahidi |
| 2003/0097055 A1 | 5/2003 | Yanof et al. |
| 2003/0171672 A1 | 9/2003 | Varghese et al. |
| 2003/0171680 A1 | 9/2003 | Paltieli |
| 2004/0010190 A1 | 1/2004 | Shahidi |
| 2004/0152970 A1 | 8/2004 | Hunter et al. |
| 2004/0167389 A1 | 8/2004 | Brabrand |
| 2004/0176690 A1 | 9/2004 | Brabrand |
| 2004/0220562 A1 | 11/2004 | Garabedian et al. |
| 2005/0041843 A1 | 2/2005 | Sawyer |
| 2005/0085793 A1 | 4/2005 | Glossop |
| 2005/0113816 A1 | 5/2005 | Whitmore, III et al. |
| 2005/0177054 A1 | 8/2005 | Yi et al. |
| 2005/0182319 A1 | 8/2005 | Glossop |
| 2005/0184988 A1 | 8/2005 | Yanof et al. |
| 2005/0267359 A1 | 12/2005 | Hussaini et al. |
| 2006/0020279 A1 | 1/2006 | Chauhan et al. |
| 2006/0052693 A1 | 3/2006 | Tynes et al. |
| 2006/0089624 A1 | 4/2006 | Voegele et al. |
| 2006/0122497 A1 | 6/2006 | Glossop |
| 2006/0149147 A1 | 7/2006 | Yanof |
| 2006/0173269 A1 | 8/2006 | Glossop |
| 2006/0173291 A1 | 8/2006 | Glossop |
| 2006/0184016 A1 | 8/2006 | Glossop |
| 2006/0241368 A1 | 10/2006 | Fichtinger et al. |
| 2007/0016067 A1 | 1/2007 | Webster, III et al. |
| 2007/0032723 A1 | 2/2007 | Glossop |
| 2007/0049820 A1 | 3/2007 | Stern et al. |
| 2007/0055128 A1 | 3/2007 | Glossop |
| 2007/0060790 A1 | 3/2007 | Kura et al. |
| 2007/0066881 A1 | 3/2007 | Edwards et al. |
| 2007/0078334 A1 | 4/2007 | Scully et al. |
| 2007/0167787 A1 | 7/2007 | Glossop et al. |
| 2007/0167806 A1 | 7/2007 | Wood et al. |
| 2007/0197896 A1 | 8/2007 | Moll et al. |
| 2007/0232882 A1 | 10/2007 | Glossop et al. |
| 2008/0004481 A1 | 1/2008 | Bax et al. |
| 2008/0009791 A1 | 1/2008 | Cohen et al. |
| 2008/0015677 A1 | 1/2008 | Glossop et al. |
| 2008/0033417 A1 | 2/2008 | Nields et al. |
| 2008/0033418 A1 | 2/2008 | Nields et al. |
| 2008/0033419 A1 | 2/2008 | Nields et al. |
| 2008/0033420 A1 | 2/2008 | Nields et al. |
| 2008/0071215 A1 | 3/2008 | Woods et al. |
| 2008/0091101 A1 | 4/2008 | Velusamy et al. |
| 2008/0125649 A1 | 5/2008 | Meyer et al. |
| 2008/0132797 A1 | 6/2008 | Brabrand |
| 2008/0200798 A1 | 8/2008 | Eklund et al. |
| 2008/0200806 A1 | 8/2008 | Liu et al. |
| 2008/0221520 A1 | 9/2008 | Nagel et al. |
| 2008/0281181 A1 | 11/2008 | Manzione et al. |
| 2008/0298655 A1 | 12/2008 | Edwards |
| 2008/0312561 A1 | 12/2008 | Chauhan |
| 2009/0036900 A1 | 2/2009 | Moll |
| 2009/0082784 A1 | 3/2009 | Meissner et al. |
| 2009/0088897 A1 | 4/2009 | Zhao et al. |
| 2009/0112119 A1 | 4/2009 | Kim |
| 2009/0149867 A1 | 6/2009 | Glozman et al. |
| 2009/0171244 A1 | 7/2009 | Ning et al. |
| 2009/0198093 A1 | 8/2009 | Meissner et al. |
| 2009/0221908 A1 | 9/2009 | Glossop |
| 2009/0221999 A1 | 9/2009 | Shahidi |
| 2009/0248041 A1 | 10/2009 | Williams et al. |
| 2009/0281566 A1 | 11/2009 | Edwards et al. |
| 2009/0306471 A1 | 12/2009 | Gettman |
| 2009/0326365 A1 | 12/2009 | Goldenberg et al. |
| 2010/0016710 A1 | 1/2010 | Kumar et al. |
| 2010/0063496 A1 | 3/2010 | Trovato et al. |
| 2010/0185087 A1 | 7/2010 | Nields et al. |
| 2010/0217117 A1 | 8/2010 | Glossop et al. |
| 2010/0234856 A1 | 9/2010 | Stoianovici et al. |

(56) References Cited

U.S. PATENT DOCUMENTS

| | | |
|---|---|---|
| 2010/0305446 A1 | 12/2010 | Berard-Anderson et al. |
| 2011/0021922 A1 | 1/2011 | Berard-Anderson et al. |
| 2011/0054309 A1 | 3/2011 | Edwards |
| 2011/0184276 A1 | 7/2011 | Lyon et al. |
| 2011/0196385 A1 | 8/2011 | Altrogge et al. |
| 2011/0208044 A1 | 8/2011 | Edwards et al. |
| 2011/0257522 A1 | 10/2011 | Berard-Anderson et al. |
| 2012/0022368 A1 | 1/2012 | Brabrand et al. |
| 2012/0046521 A1 | 2/2012 | Hunter et al. |
| 2012/0059220 A1 | 3/2012 | Holsing et al. |
| 2012/0059248 A1 | 3/2012 | Holsing et al. |
| 2012/0071753 A1 | 3/2012 | Hunter et al. |
| 2012/0158047 A1 | 6/2012 | Edwards et al. |
| 2012/0190970 A1 | 7/2012 | Velusamy et al. |

FOREIGN PATENT DOCUMENTS

| | | |
|---|---|---|
| EP | 1791070 A2 | 5/2007 |
| EP | 1534153 B1 | 4/2009 |
| WO | WO 99/00052 A1 | 1/1999 |
| WO | WO 02/24051 A2 | 3/2002 |
| WO | WO 03/091839 A2 | 11/2003 |
| WO | WO 2004/086974 A1 | 10/2004 |
| WO | WO 2009/092059 A2 | 7/2009 |
| WO | WO 2009/144730 A1 | 12/2009 |
| WO | WO 2009/157007 A1 | 12/2009 |
| WO | WO 2010/084322 A1 | 7/2010 |
| WO | WO 2011/135288 A2 | 11/2011 |

OTHER PUBLICATIONS

Wood, B. et al., "CT-guided interventional oncology: bridging the gap between diagnosis and therapy," MedicaMundi, vol. 49, No. 3, Nov. 2005; 5 pages.

Rieder, C. et al., "Visualization of Risk Structures for Interactive Planning of Image Guided Radiofrequency Ablation of Liver Tumors," Fraunhofer MEVIS, Institute for Medical Image Computing, Mar. 13, 200; 9 pages.

Damianou, C. et al., "Positioning device for MRI-guided high intensity focused ultrasound system," Int J CARS, Jan. 17, 2008, 11 pages.

Leong, F. et al., "A Precise Robotic Ablation and Division Mechanism for Liver Resection," Lecture Notes in Computer Science, 2008, vol. 5128/2008, Abstract.

Duan, X. et al., "A medical robot for needle placement therapy in liver cancer," Journal of Zhejiang University Science, 2010, vol. 11, No. 4. Abstract.

Freschi, C., "Ultrasound guided robotic biopsy using augmented reality and human-robot cooperative control." Conf Proc IEEE Eng Med Biol Soc, 2009; 2009:5110-3, Abstract.

Hata, N. et al., "MRI-Compatible Manipulator With Remote-Center-of-Motion Control," J Magn Reson Imaging, May 2008, vol. 27, No. 5, 21 pages.

Rovetta, A., "Tests on reliability of a prostate biopsy telerobotic system." Stud Health Technol Inform., 1999; vol. 62, Abstract.

Meier-Meitinger, M. et al., "Computer-assisted navigation system for interventional CT-guided procedures: results of phantom and clinical studies." Rofo. Apr. 2008, vol. 180, No. 4, Abstract.

Peng, C., et al., "Robot Assisted Needle Placement: Developed Using Image Guided Surgery Toolkit (IGSTK)," Jul. 10, 2006, 8 pages.

Barrett, S. et al., "A Remote Needle Guidance System for Percutaneous Biopsies," Proceedings of IDETC/CIE 2005, Sep. 2005, 9 pages.

Maurin, B. et al., "A Patient-Mounted Robotic Platform for CT-scan Guided Procedures," IEEE Transactions on Biomedical Engineering, published at least as early as Feb. 16, 2010, 8 pages.

McCreedy, E. et al., "Radio Frequency Ablation Registration, Segmentation, and Fusion Tool," IEEE Trans Int Technol Biomed., Jul. 2006, vol. 10, No. 3, 16 pages.

Kettenbach, J. et al., "Robot-Assisted Biopsy Using Computed Tomography-Guidance," Investigative Radiology, vol. 40, No. 4, Apr. 2005, pp. 219-228.

U.S. Appl. No. 13/292,327, entitled "Systems and Methods for Planning Image Guided Interventional Procedures," filed Nov. 9, 2011.

U.S. Appl. No. 13/435,980, entitled "Systems and Methods for Planning Image Guided Interventional Procedures," filed Mar. 30, 2012.

Office Action for U.S. Appl. No. 11/682,375, mailed on Jul. 14, 2009; 12 pages.

Final Office Action for U.S. Appl. No. 11/682,375, mailed on Dec. 28, 2009; 14 pages.

Office Action for U.S. Appl. No. 11/682,375, mailed on Jan. 27, 2012; 12 pages.

Final Office Action for U.S. Appl. No. 11/682,375, mailed on Jul. 30, 2012; 15 pages.

\* cited by examiner

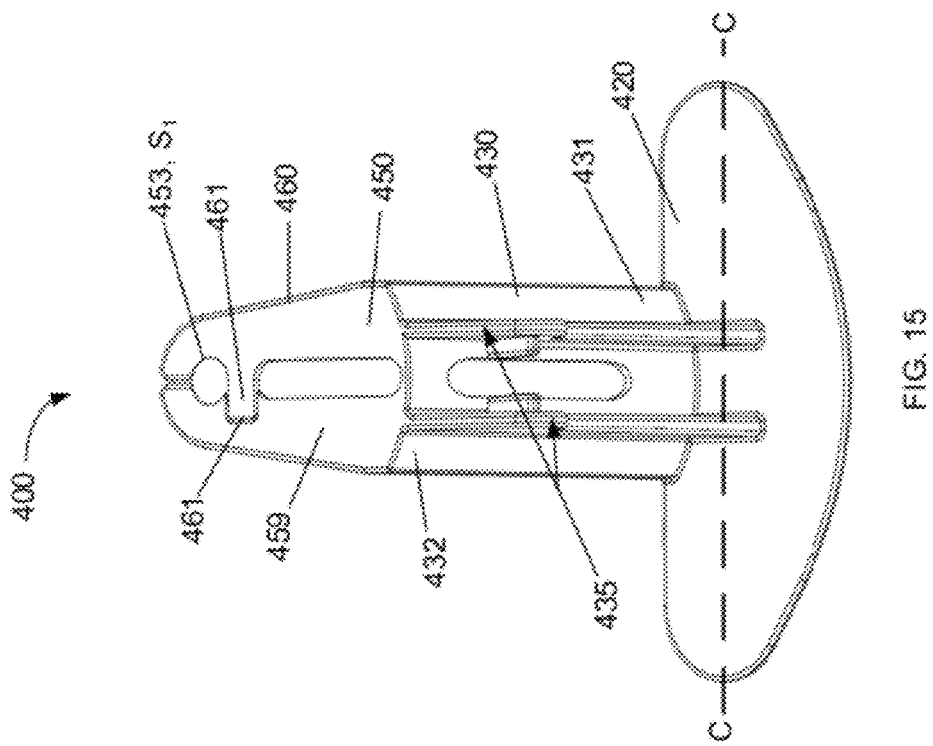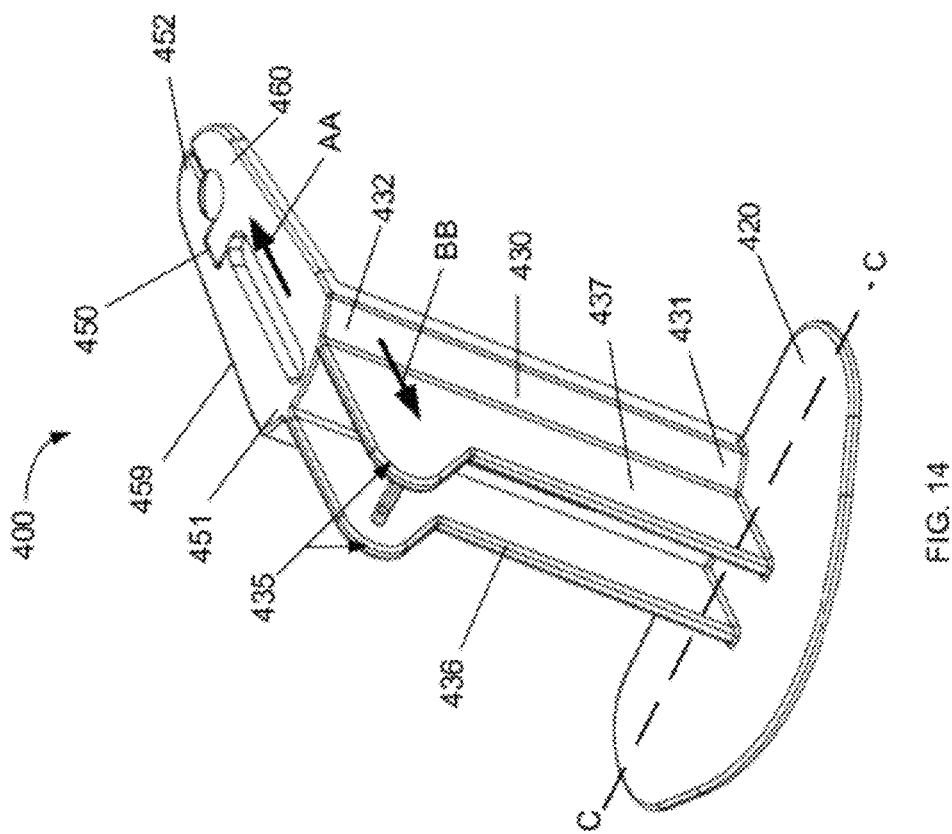

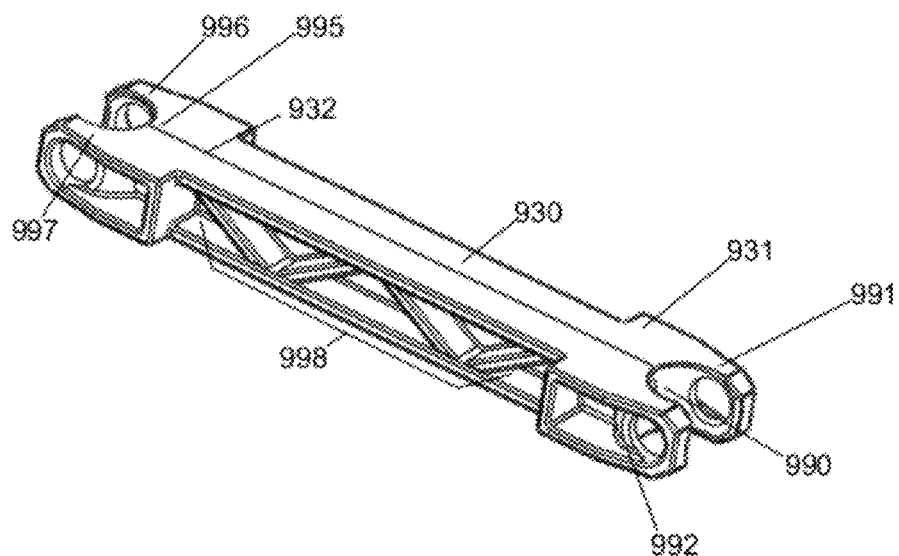
FIG. 30
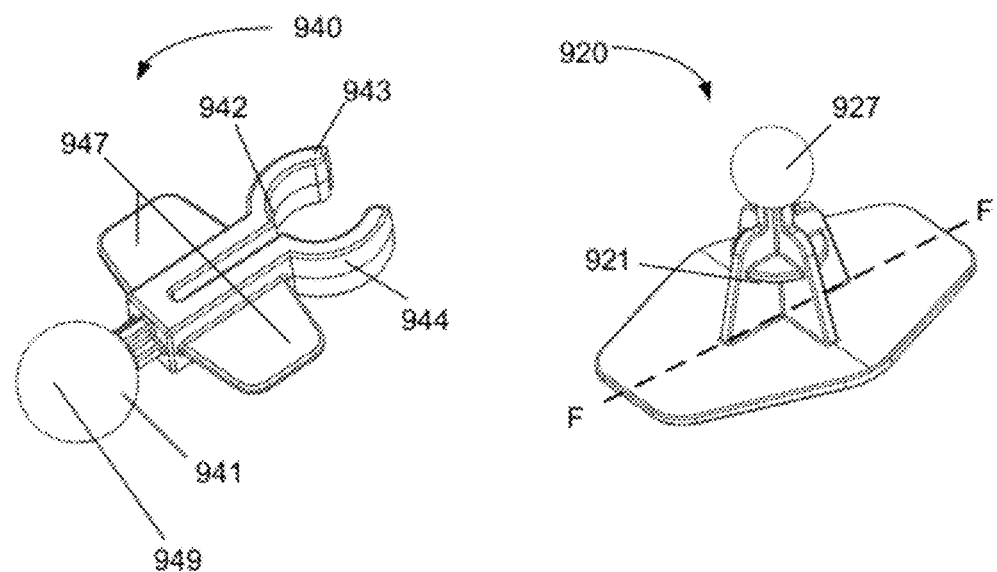
FIG. 31
FIG. 32

APPARATUS AND METHOD FOR STABILIZING A NEEDLE

CROSS-REFERENCE TO RELATED APPLICATIONS

This application is a continuation application of U.S. patent application Ser. No. 13/292,186, entitled "Apparatus and Method for Stabilizing a Needle," filed Nov. 9, 2011, which claims priority to and the benefit of Indian Provisional Patent Application No. 3363/CHE/2010, entitled "Apparatus and Method for Stabilizing a Needle," filed Nov. 10, 2010, and Indian Non-provisional Patent Application No. 3363/CHE/2010, entitled "Apparatus and Method for Stabilizing a Needle," filed Aug. 19, 2011, the disclosures of which are hereby incorporated by reference in their entirety.

BACKGROUND

The invention relates generally to medical devices and more particularly to an apparatus for use in stabilizing a tool during an image-guided interventional procedure.

Some known interventional procedures generally require the tool, such as a needle, to remain stable at the target after the tool has been positioned using an image-guided device. Needle stabilization can facilitate accuracy of the interventional procedure. Such needle stabilization can be a concern, especially in longer procedures such as ablation. During longer procedures, a needle inserted at the target can tend to move away from the target due to tissue sagging, movement of tissues due to respiratory movement, etc. At the same time, it can be required that the needle be allowed enough freedom such that the patient is not uncomfortable, and there is no tissue damage due to extremely rigid positioning of the needle. Further, some robotic interventional procedures require multiple needles to be placed close to each other. The device used for stabilization of one needle can hinder the placement of another needle very close to the placement of the needle and its stabilizing device.

Furthermore, stabilization devices typically allow the needle to be stabilized at a particular penetration level. Generally, the robotic placement of the needle and the stabilization device are independent apparatus and methods. After the needle is robotically placed at the target, the penetration level of the needle can be fixed and a stabilization device can be used to stabilize the needle at the same penetration level. There is typically no provision for altering the penetration level and checking the needle placement at a lower penetration level. There is also typically no provision for movement of the needle during a long duration procedure, such as with an ablation procedure.

Thus, a need exists for a stabilization device that can be used during an interventional procedure to stabilize the position of a tool (e.g., an ablation needle) after the tool has been positioned at a desired entry point on the patient.

SUMMARY OF THE INVENTION

Apparatus and methods for use in an image-guided interventional procedure are described herein. In one embodiment, an apparatus includes a base configured to be releasably coupled to a patient's skin. The base defines a longitudinal axis. A support portion extends from the base at an angle transverse to a longitudinal axis defined by the base. The support portion has a first end portion and a second end portion. The first end portion is disposed adjacent the base. A holder portion extends from the second end portion of the support portion. The holder portion defines an opening and is configured to be moved between a first configuration, in which the opening defined by the holder portion has a first size and is configured to movably receive an interventional tool therethrough, and a second configuration, in which the opening defined by the holder portion has a second size different than the first size.

BRIEF DESCRIPTION OF THE DRAWINGS

FIG. 14 is a side perspective view of a stabilization device, according to another embodiment.

FIG. 15 is a rear view of the stabilization device of FIG. 14, shown with the holder portion in a first configuration.

FIG. 30 is an enlarged perspective view of a base of the stabilization device of FIG. 28.

FIG. 31 is an enlarged perspective view of a clamp member of the stabilization device of FIG. 28.

FIG. 32 is an enlarged perspective view of a support member of the stabilization device of FIG. 28.

DETAILED DESCRIPTION

Figure 1:
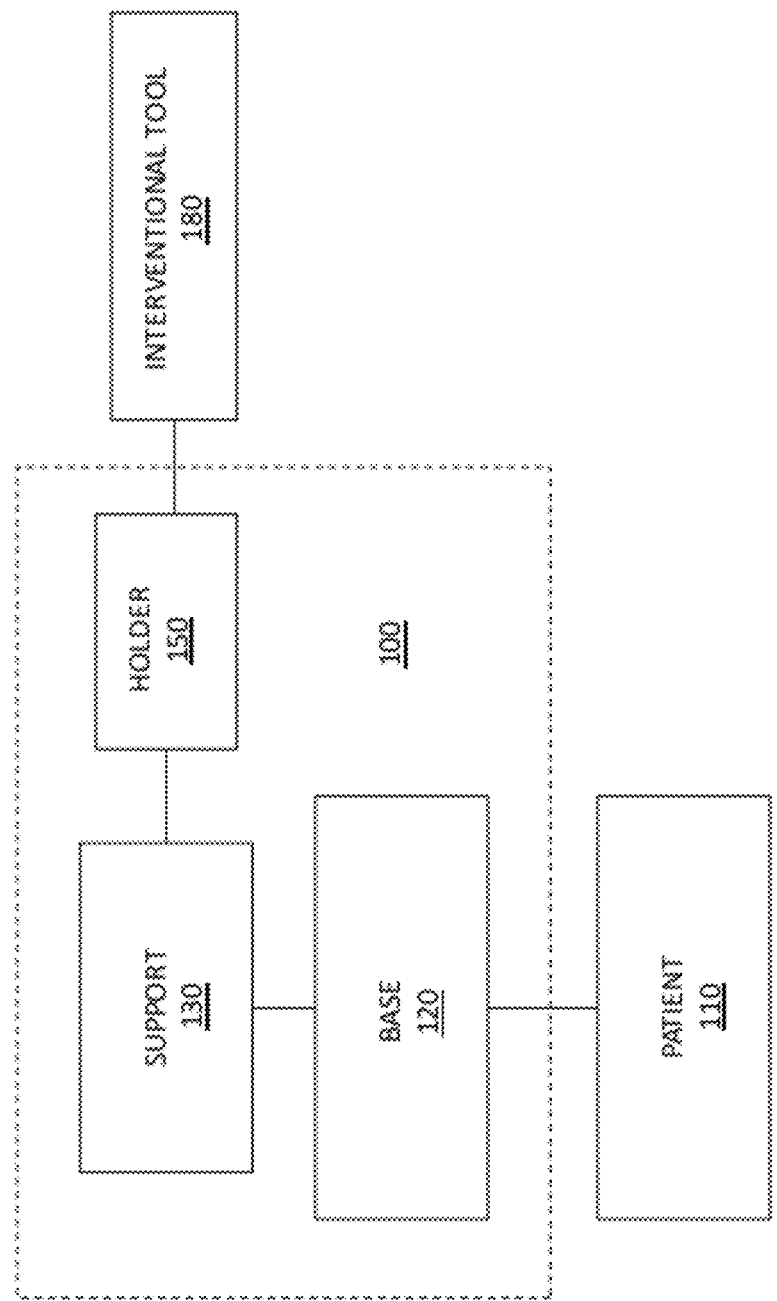
FIG. 1 is a schematic illustration of a stabilization device, according to an embodiment.

Apparatus and methods are described herein that can be used during an image-guided interventional procedure, such as, for example, an image-guided needle ablation procedure. A stabilization device described herein can be attached to a patient's skin and used to stabilize an interventional tool during such in interventional procedure. In some embodiments, the stabilization device can be configured to adjust an opening size through which an interventional tool (e.g., an ablation needle) can be received. In some embodiments, a stabilization device can include a removable holder member that can be releasably coupled to a tool guide of an image-guided interventional device, and releasably coupled to a portion of the stabilization device.

In some embodiments, an apparatus includes a base configured to be releasably coupled to a patient's skin. The base defines a longitudinal axis. A support portion extends from the base at an angle transverse to a longitudinal axis defined by the base. The support portion has a first end portion and a second end portion. The first end portion is disposed adjacent the base. A holder portion extends from the second end portion of the support portion. The holder portion defines an opening and is configured to be moved between a first configuration, in which the opening defined by the holder portion has a first size and is configured to movably receive an interventional tool therethrough, and a second configuration, in which the opening defined by the holder portion has a second size different than the first size.

In some embodiments, an apparatus includes a base configured to be releasably coupled to a patient's skin and a support portion that extends from the base at an angle transverse to a longitudinal axis defined by the base. The support portion can have a first end portion and a second end portion. The first end portion can be disposed adjacent the base. A holder portion extends from the second end portion of the support portion in a first direction and the holder portion defines an opening configured to receive an interventional tool therethrough. A first rib member extends from the support portion in a second direction opposite the first direction, and a second rib member extends from the support portion in the second direction. The first rib member and the second rib member each can be pivotally movable relative to the support portion from a first configuration in which the first rib member and the second rib member are substantially parallel to each other and the opening defined by the holder portion has a first size, and a second configuration in which the first rib member and the second rib member are each pivoted relative to the support portion and the opening defined by the holder portion has a second size greater than the first size.

In some embodiments, an apparatus includes a base configured to be releasably coupled to a patient's skin. An elongate support member is coupled to the base. The elongate support member has a first end portion and a second end portion and the first end portion is coupled to the base. A holder member is releasably couplable to the second end portion of the elongate support member and is configured to be coupled to a tool guide during an image guided interventional procedure. The holder member is configured to be movable from a first position in which the holder member is coupled to the tool guide and the tool guide is configured to guide an interventional tool during an image guided interventional procedure at a predetermined angle relative to the patient's body, and a second position in which the holder member is coupled to the elongate support member and is configured to stabilize the interventional tool at the predetermined angle relative to the patient's body.

In some embodiments, a method includes guiding an interventional tool at a predetermined angle relative to a patient's body using a holder member coupled to an image-guided positioning device ("IGPD") during an interventional procedure such that a distal end of the interventional tool extends through an opening defined in a stabilization device and is disposed at a first position. The stabilization device includes a base and an elongate shaft coupled to the base. The holder member is released from the IGPD. The holder member is releasably coupled to the stabilization device. A position of the interventional tool relative to the patient's body is verified using image information of the patient's body and the interventional tool. The stabilization device is releasably coupled to the patient's body and the interventional tool is moved such that the distal end of the interventional tool penetrates the patient's body and is disposed at a second position.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the end of a needle inserted inside a patient's body would be the distal end of the needle, while the end outside a patient's body would be the proximal end of the needle.

As used herein, a "set" can refer to multiple features or a singular feature with, for example, multiple parts. For example, when referring to set of flanges, the set of flanges can be considered as one flange with two distinct protrusions, or the set of flanges can be considered as multiple flanges.

FIG. 1 is a schematic illustration of a stabilization device according to an embodiment. A stabilization device 100 can be used in conjunction with an image-guided tool guide device (not shown), such as for example a device used to position and/or insert an interventional medical tool 180 (also referred to herein as "medical tool" or "interventional tool") into a patient's body 110. Such an interventional tool 180 can be, for example, an ablation needle. An image-guided tool guide device can be used to perform a variety of different medical procedures that include the insertion of a medical tool 180 at a desired location within a patient's body. For example, an image-guided tool guide device can be used to insert an ablation needle into a patient's body that is used to ablate a tumor within the patient. The image-guided tool guide device can be configured to determine a desired angle and depth of insertion for the interventional tool. In some embodiments, the image-guided tool guide device can be automated or robotic and can be configured to automatically position or insert the interventional medical tool 180 at a desired treatment site. In some embodiments, the image-guided tool guide device can be partially automated and be used in conjunction with manual functions performed by a clinician (e.g., a physician) performing the particular procedure. For example, the image-guided tool guide device can determine the appropriate angle and depth of insertion of an interventional tool 180, and the clinician can manually insert the interventional tool based on the determined angle and depth.

In such image-guided interventional procedures, during and/or after the insertion of the interventional tool 180 it may be desirable to stabilize the interventional tool 180 at the target treatment site. For example, in some procedures, after the interventional medical tool 180 has been inserted into the patient's body 110, at least a portion of the interventional tool 180 can sag due to factors, such as, for example, the weight of the interventional tool. If the interventional tool 180 sags during a procedure, it can undesirably alter the position of the working end (distal end) of the interventional tool 180 relative to the patient. The stabilization device 100 described herein can be used to stabilize or maintain the desired position of the interventional tool 180 during the interventional procedure. For example, the stabilization device 100 can be releasably coupled to the patient's body 110, such as for example, to the patient's skin. After the image-guided tool guide device has determined the desired angle and depth of insertion for the interventional tool 180, the interventional tool 180 can be moved along the insertion trajectory and then coupled to the stabilization device 100 prior to penetration of the interventional tool 180 into the patient's body. In some embodiments, the interventional tool 180 can be coupled to the stabilizing device 100 after the interventional tool 180 has been inserted into the patient's body.

In some embodiments, the stabilization device 100 provides the interventional tool 180 with sufficient freedom of movement together with an appropriate amount of physician defined clearance area. Such control and flexibility of the clearance area during stabilization of the interventional tool 180 can provide patient comfort during the procedure, limit or prevent unnecessary tissue damage, and/or reduce placement errors associated with the placement of the interventional tool relative to a tissue area (e.g., a tumor) to be treated. In some embodiments, multiple stabilization devices 100 can be used to place multiple interventional tools 180 in the patient in close proximity to each other.

In some embodiments, the penetration of the interventional tool 180 can be altered using the stabilization device 100. For example, in some embodiments, a check of the placement of the interventional tool 180 using an imaging device (not shown) can be performed with a distal end of the interventional tool 180 disposed at a first position relative to the patient. The interventional tool 180 can then be inserted further into the tissue using the stabilization device 100 as described in more detail below with reference to specific embodiments.

As shown in FIG. 1, the stabilization device 100 can include a base 120, a holder portion 150 (also referred to herein as "holder member" or "holder"), and a support portion (also referred to herein as "support member" or "support") 130. The base 120 of the stabilization device 100 can be releasably coupled to a patient's skin with, for example, adhesive or with a suction pad using suction force to hold the base 120 in position on the patient 110. In some embodiments, the support portion 130 extends from the base 120 at an angle transverse to a longitudinal axis defined by the base 120. For example, the support portion 120 can have a first end portion and a second end portion, and the first end portion can be disposed adjacent the base 120 and the second end portion can extend away from the base 120 at an angle relative to the base 120. In some embodiments, the first end portion of the support portion 130 is pivotally coupled to the base 120.

In some embodiments, the support portion 130 is formed monolithically and/or integrally with the base 120. In some embodiments, the support portion 130 can be a separate component coupled to the base 120. The support portion 130 can include, for example, an elongate shaft and can have a cross-section that is circular, square, elliptical, rectangular, or any other suitable cross-section. The support portion 130 can be formed as a solid component or can include a lumen or passageway through at least a portion of the support portion 130.

In some embodiments, the holder portion 150 extends from the second end portion of the support portion 130. In some embodiments, the holder portion 150 is configured to be coupled to the support portion 130 with a clamp member (not shown in FIG. 1). The holder portion 150 defines an opening that can receive at least a portion of the interventional tool 180 therethrough. The holder portion 150 can be configured to be moved between a first configuration in which the opening defined by the holder portion 150 has a first size and is configured to movably receive an interventional tool therethrough, and a second configuration in which the opening defined by the holder portion 150 has a second size different than the first size. In some embodiments, the holder portion 150 when in the second configuration is configured to releasably maintain the interventional tool 180 within the opening of the holder portion 150.

In some embodiments, the holder portion 150 includes a first holder arm (not shown in FIG. 1) and a second holder arm (not shown in FIG. 1) that collectively define the opening. In some embodiments, the support portion 130 includes a grip member (not shown) configured to move the first holder arm and the second holder arm between a first configuration and a second configuration. For example, in some embodiments, in the first configuration, the first holder arm and the second holder arm are substantially closed such that an interventional tool 180 disposed within the opening is not permitted to be moved out of the opening in a lateral direction, and in the second configuration, the first holder arm and the second holder arm are spread apart a distance sufficient to allow the interventional tool 180 to be laterally moved out of the opening.

In some embodiments, the holder portion 150 can extend from the second end portion of the support portion 130 in a first direction and the grip member extends from the support portion 130 in a second direction opposite the first direction. The grip member can include a first rib member and a second rib member each extending from the support portion 130 in the second direction. The first rib member and the second rib member can each be pivotally movable relative to the support portion 130 from a first configuration in which the first rib member and the second rib member are substantially parallel to each other and the opening defined by the holder portion 150 has a first diameter or size, and a second configuration in which the first rib member and the second rib member are each pivoted relative to the support portion 130 and the opening defined by the holder portion 150 has a second diameter or size greater than the first diameter or size. In some embodiments, when the first rib member and the second rib member are in the first configuration, the holder portion 150 can be configured to releasably maintain the interventional tool 180 within the opening of the holder portion 150.

In some embodiments, the stabilization device 100 can include an adjustment mechanism (not shown) that is coupled to the holder portion 150. The adjustment mechanism can be configured to be moved between a first configuration in which an opening defined by the adjustment mechanism is a first size and a second configuration in which the opening has a second size different from the first size. The opening of the adjustment mechanism can be disposed in at least a partially overlying relation with the opening defined by the holder portion 150, such that when the adjustment mechanism is moved between its first configuration and its second configuration the size of the opening of the holder portion 150 can be effectively changed. In other words, the size of the opening of the holder portion 150 in which an interventional tool can be inserted can be selectively changed using the adjustment mechanism.

In some embodiments, the holder portion 150 includes an adjustment portion (not shown in FIG. 1) monolithically or integrally formed therewith that can be configured to selectively adjust the size of the opening defined by the holder portion 150 between multiple different sizes. For example, the holder portion 150 can include a ratcheting portion that includes teeth that can be moved to secure the holder portion 150 at a desired position having a desired opening size configured to receive the interventional tool 180 therethrough.

In some embodiments, the holder portion 150 can be releasably coupled to the second end portion of the support portion 130 and can be releasably coupled to an image-guided tool guide. In some embodiments, a clamp member can be coupled to the second end portion of the support portion 130, and the holder portion 150 can be releasably coupled to the clamp member. In some embodiments, the clamp member can be pivotally coupled to the second end portion of the support portion 130, such that when the holder portion 150 is coupled to the clamp member, the clamp member and the holder portion 150 are collectively pivotally movable relative to the support portion 130. In such an embodiment, the holder portion 150 can be movable from a first position in which the holder portion 150 is coupled to the tool guide of an IGPD and the interventional tool 180 can be disposed at a predetermined angle relative to the patient's body, and a second position in which the holder portion 150 is coupled to the support portion 130 and can be used to stabilize the interventional tool 180 at the predetermined angle relative to the patient's body 110.

FIGS. 2-9 illustrate a stabilization device 200 according to an embodiment. The stabilization device 200 includes a base 220, a support member 230, a clamp member 240, and a holder member 250. As described above for stabilization device 100, the stabilization device 200 can be used to provide support (i.e., stabilization) to an interventional tool 280 (shown in FIGS. 7-9) during an interventional procedure, such as for example, a procedure to treat a tumor within a patient. The base 220 of the stabilization device 200 can be releasably coupled to the patient with, for example, an adhesive, with suction force, or other suitable coupling method. For example, the base 220 can be releasably coupled to the skin of a patient. In some embodiments, the base 220 includes a medical grade adhesive on a bottom surface of the base 220 that can be used to adhere the base 220 to the patient's skin. The base 220 can have a variety of different suitable shapes and/or sizes such that appropriate adhesion and/or suction can occur. For example, the base 220 can be substantially octagonal, circular, square, elliptical, or oblong and/or can be configured such that the footprint of the base 220 is minimized reducing interference with other devices (e.g. a second stabilization device) and/or interference with clinicians performing the interventional procedure (e.g., physicians).

Figure 4:
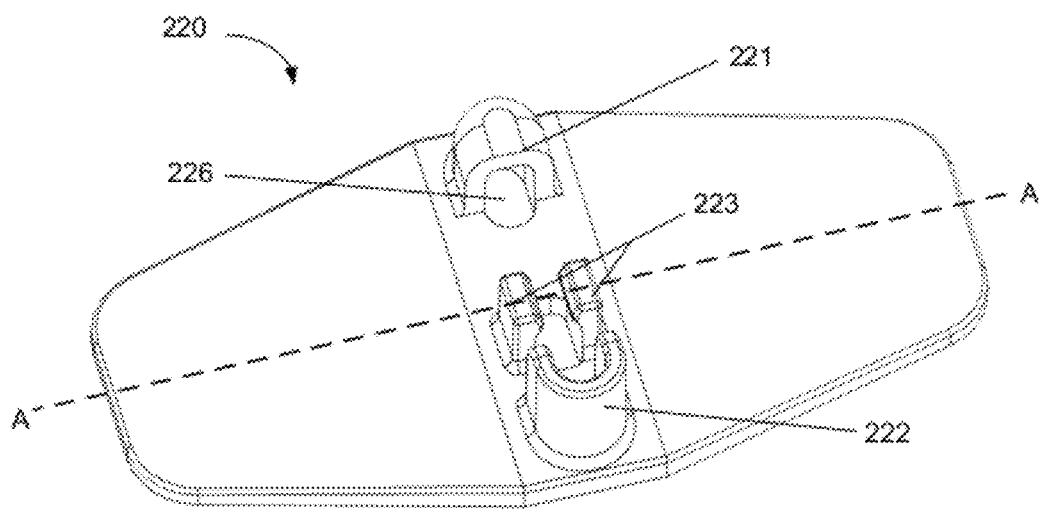
FIG. 4 is an enlarged perspective view of a base of the stabilization device of FIG. 2.

The base 220 includes a coupling portion 225 that can be used to couple the support member 230 thereto. As shown in FIG. 4, the coupling portion 225 can include a first coupling member 221, a second coupling member 222, and a third coupling member 223 used to couple the support member 230 to the base 220. More specifically, the coupling member 221 defines an aperture 226 that can receive an end portion of an extension 238 (see e.g., FIG. 5) of the support member 230. The second coupling member 222 defines a pocket or channel (e.g., a u-shaped cutout) that can receive a first end portion 231 of the support member 230. The third coupling member 223 can be formed with two opposed upstanding walls that receive between them a second portion of the extension 238 and, as such, create a snap fit with the extension 238. For example, the walls of the third coupling member 223 can be flexible such that they can flex apart from each other to allow the extension 238 to be inserted therein.

The support member 230 includes the first end portion 231, mentioned above, and a second end portion 232. In this embodiment, the first end portion 231 includes a portion that is bent or curved, from which the support portion 230 extends at an angle transverse to a longitudinal axis A defined by the base 220, as shown, for example, in FIG. 3. Thus, the support portion 230 includes an extension 238 that can be disposed adjacent to the base 220 and the support member 230 can extend at a desired angle relative to the base 220. In some embodiments, the angle between the support member and the base 220 can be adjustable (i.e., not fixed) and, as such, can be disposed at different positions through a range of positions. Although shown in FIGS. 2-9 as being substantially circular in cross-section, the support member 230 can have other cross-sectional shapes, such as, for example, square, rectangular, oblong, pentagonal, etc.

Figure 2:
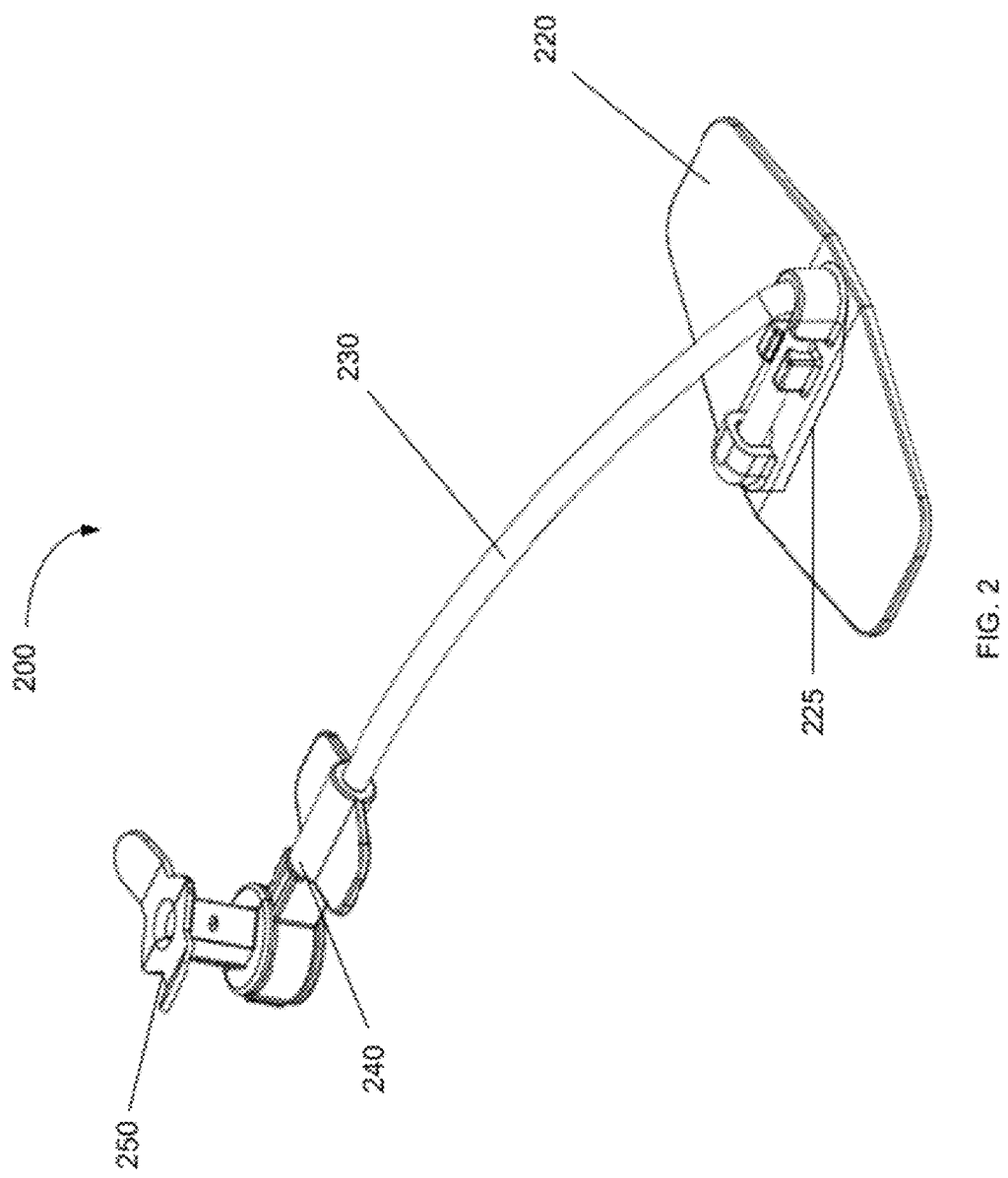
FIG. 2 is a side perspective view of a stabilization device, according to another embodiment.
Figure 3:
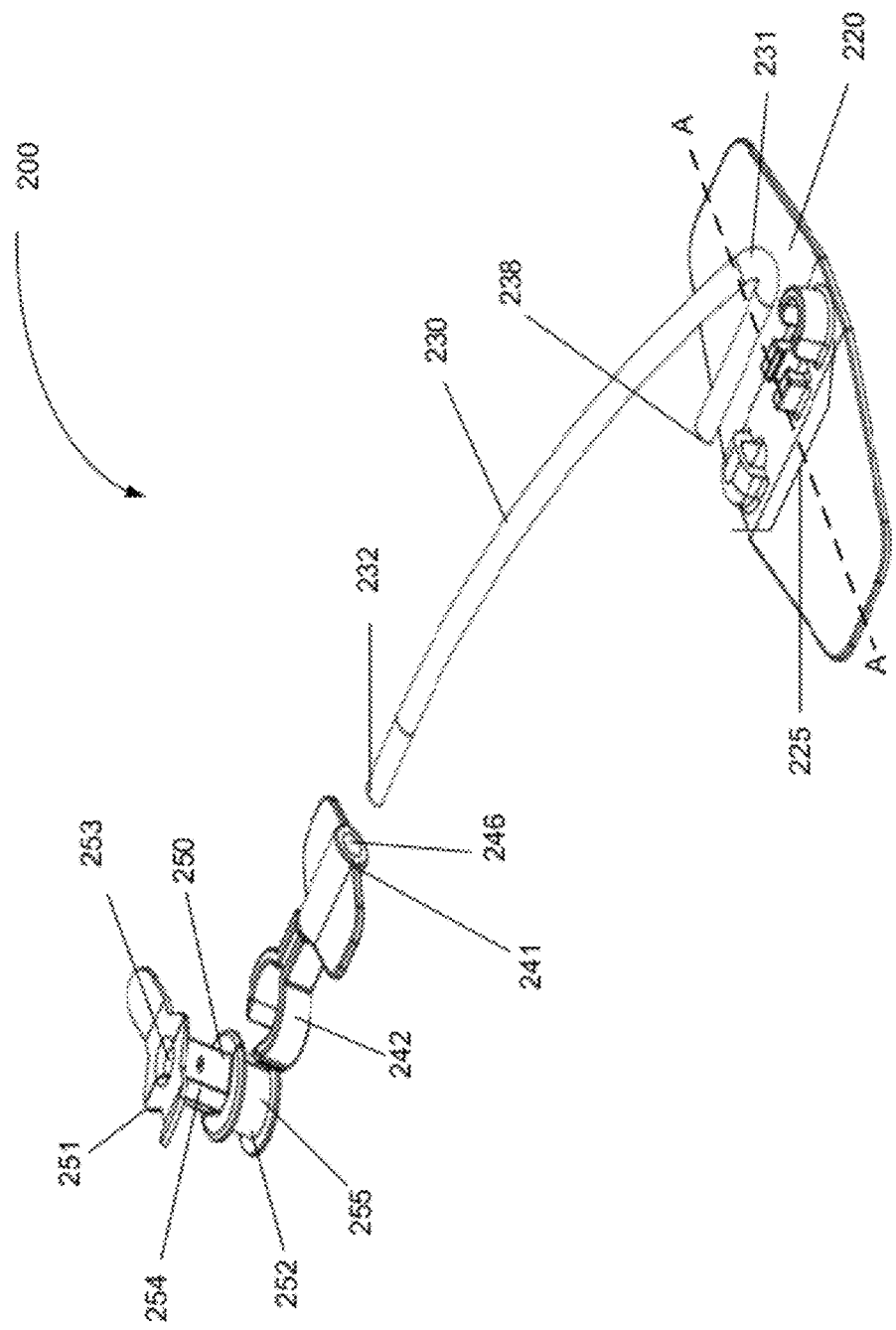
FIG. 3 is an exploded side perspective view of the stabilization device of FIG. 2.
Figure 5:
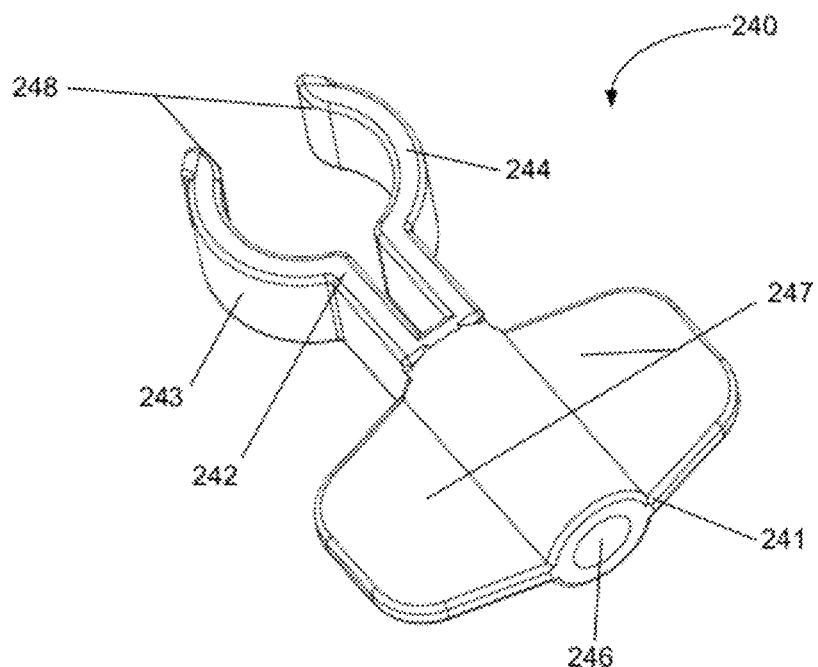
FIG. 5 is an enlarged perspective view of a clamp member of the stabilization device of FIG. 2.

The clamping member 240 includes a first end portion 241 and a second end portion 242, and can be coupled to the support member 230 (see, e.g., FIGS. 3 and 5). More specifically, the first end portion 241 defines an aperture 246 that can receive the second end portion 232 of the support member 230. The first end portion 241 of the clamping member 240 includes a pair of wings 247, extending laterally. The wings 247 can be used, for example, to rotate the clamping member 240 relative to the second end portion 232 of the support member 230. For example, a clinician (e.g., physician) can grasp the wings 247 and rotate the clamping member 240 with respect to the support member 230. The second end portion 242 includes a first clamping arm 243 and a second clamping arm 244. The first clamping arm 243 and the second clamping arm 244 can be used to couple the clamping member 240 to the holder member 250 as shown, for example, in FIG. 2, and as described in more detail below. More particularly, the holder member 250 can be inserted (i.e., pushed) laterally through a space defined between the first clamping arm 243 and the second clamping arm 244. The first clamping arm 243 and the second clamping arm 244 can be flexible such that as the holder member 250 is inserted, the first clamping arm 243 and the second clamping arm 244 can move apart from each other. The first clamping arm 243 and the second clamping arm 244 can also each include a raised lip 248, as shown, for example, in FIG. 5, which can maintain the holder member 250 within the clamping member 240 after being inserted therein.

Figure 6:
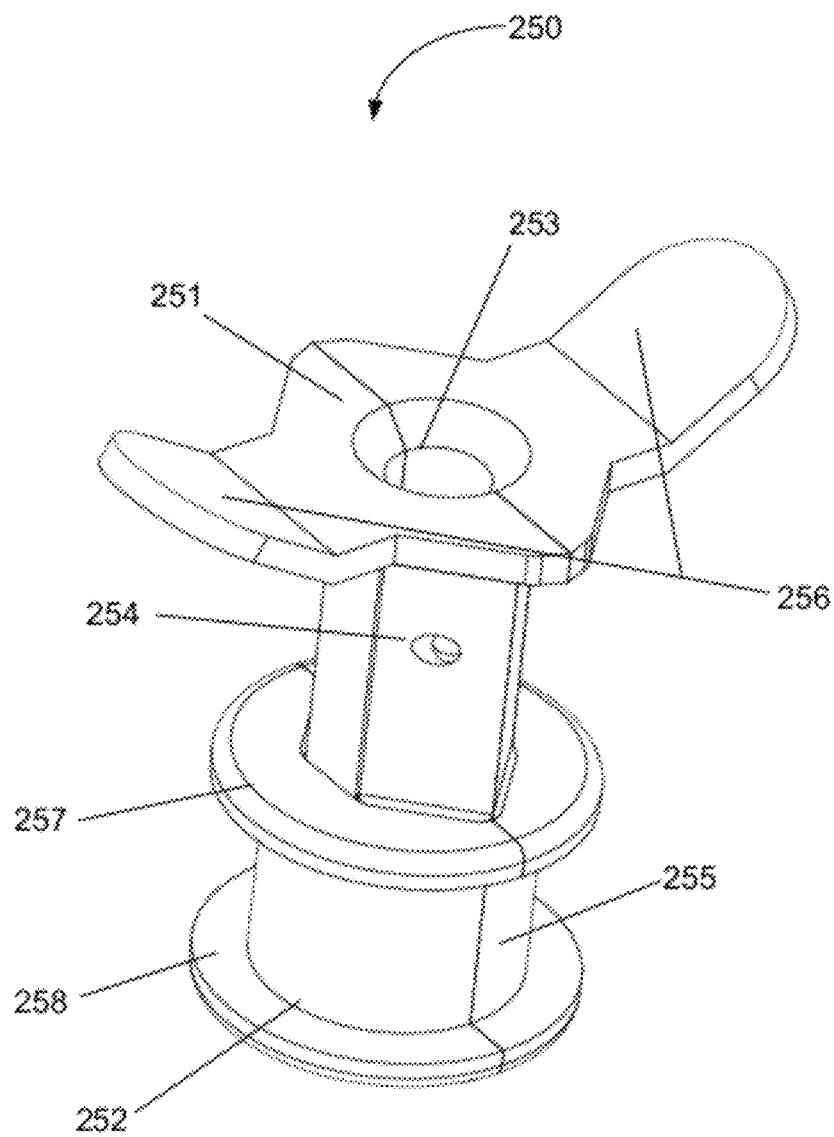
FIG. 6 is an enlarged perspective view of a holder member of the stabilization device of FIG. 2.

As shown in FIG. 6, the holder member 250 includes a first end portion 251 and a second end portion 252 and defines an opening 253 therethrough. The opening 253 is configured to receive an interventional tool 280, as shown, for example, in FIG. 7. In some embodiments, the opening 253 is sized (e.g., has a particular diameter) such that the interventional tool 280 can be movably disposed within the opening 253. In some embodiments, the opening 253 can be sized such that the interventional tool 280 can be inserted through the opening 253 and maintained at a fixed position relative to the holder member 250, e.g. by friction. In other words, the interventional tool 280 can be held in a fixed position until a force from a source other than the weight of the interventional tool 280 is applied.

Figure 7:
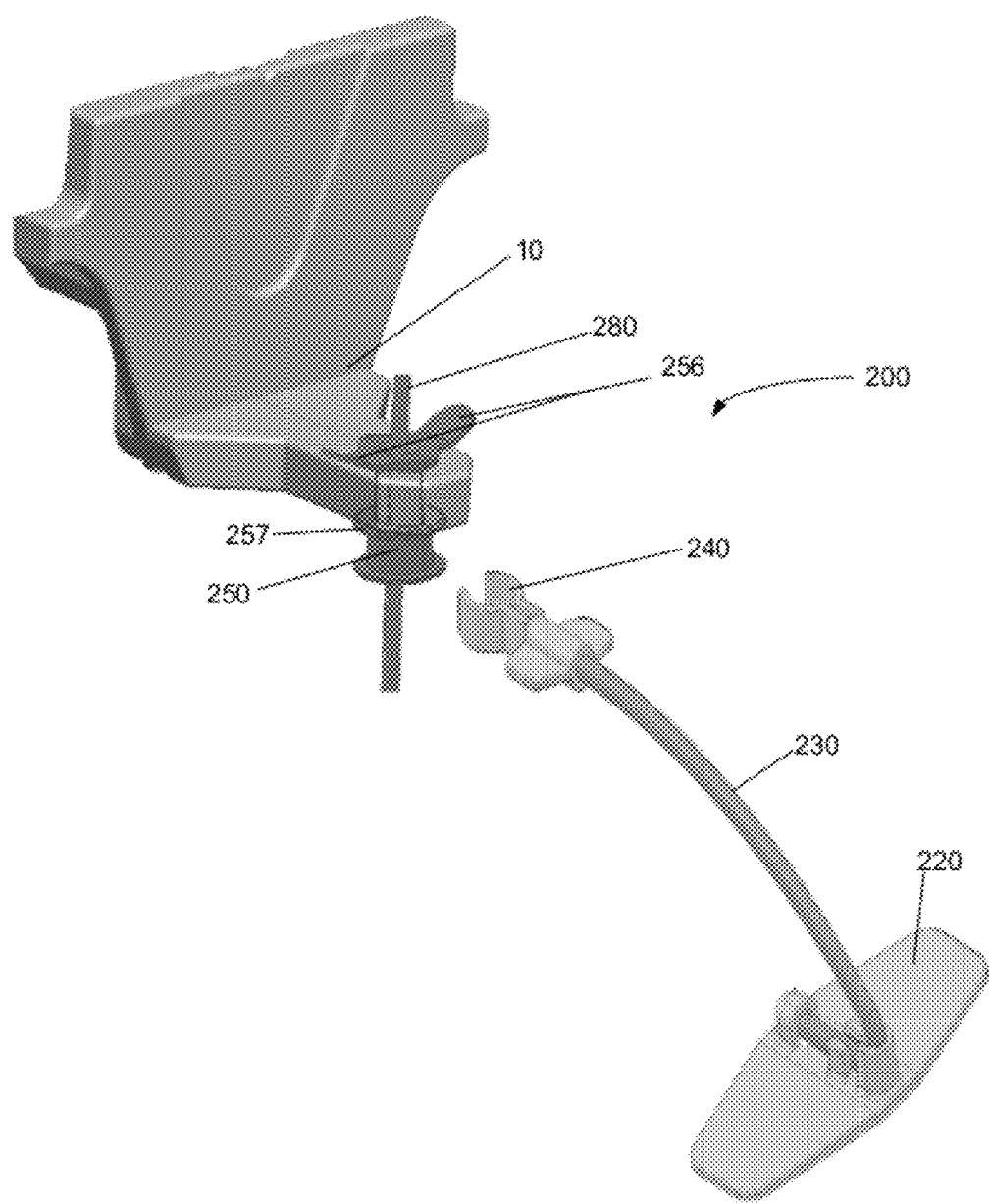
FIG. 7 illustrates the stabilization device of FIG. 2 with the holder member of the stabilization device coupled to a tool guide of an image-guided interventional device.
Figure 8:
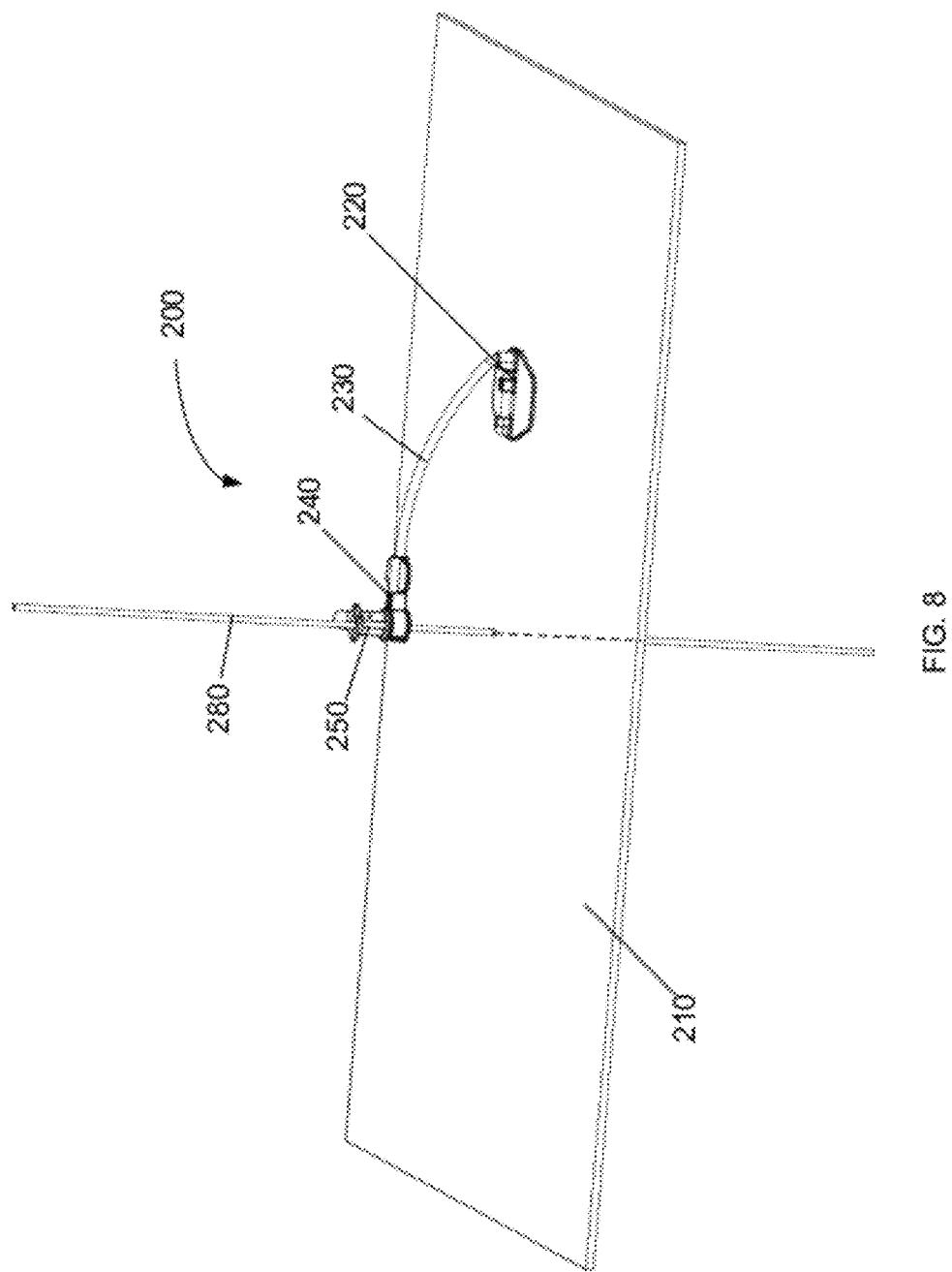
FIG. 8 is a side view of the stabilization device of FIG. 2 shown coupled to a schematic illustration of a patient's skin and an interventional tool coupled to the stabilization device and inserted through the patient's skin.

The holder member 250 can be coupled to a tool guide 10 (see e.g., FIG. 7) of an IGPD and can also be coupled to the clamping member 240 (see e.g., FIG. 2). More specifically, as shown in FIG. 7, the tool guide 10 of the IGPD can include a clamping mechanism configured to matingly receive a first recessed portion 254 (see e.g., FIG. 6) of the holder member 250. The first end portion 251 also defines a set of flanges 256 that can be used to limit the downward movement of the holder member 250 while coupled to the tool guide 10 and a top flange 257 of the second end portion 251 can be used to limit upward movement of the holder member 250, as shown, for example, in FIG. 7. In other words, the set of flanges 256 can define a surface configured to contact a top surface of the clamping mechanism of the tool guide 10, and the top flange 257 of the second end portion 252 can be configured to contact a bottom surface of the tool guide 10.

The second end portion 252 of the holder member 250 can be releasably coupled to the clamping member 240. More specifically, the first clamping arm 243 and the second clamping arm 244 of the clamping member 240 can be coupled to a second recessed portion 255 of the second portion 252 of the holder member 250, as shown in FIG. 2. As described above, the holder member 250 can be inserted (i.e., pushed) into the space defined between the first clamping arm 243 and the second clamping arm 244 of the clamping member 240. The second end portion 252 of the holder member 250 includes the top flange 257 (as described above) that can be used to limit downward movement of the holder member 250. The second end portion 252 of the holder member 250 also includes a bottom flange 258 that can be used to limit upward movement of the holder member 250 when clamped within the clamping member 240.

In use, the holder member 250 can first be coupled to the tool guide 10 during a procedure to position the interventional tool 280 at a desired position (e.g. angle and depth) relative to a patient. The holder member 250 can then be coupled to the clamping member 240 of the stabilization device 200, and released from the tool guide 10. The stabilization device 200 can be used to support or stabilize the position of the interventional tool 280 as the clinician (e.g., physician) inserts the interventional tool 280 through a patient's skin 210 and to a desired treatment site within the patient (see e.g., FIG. 8 which illustrates schematically the patient's skin 210). With the base 220 of the stabilization device 200 being coupled to the skin 210 of the patient, the stabilization device 200 can move with the patient through potential motion (i.e., breathing or relaxation of muscles). This arrangement allows the interventional tool 280 to maintain the desired angle and position relative to the patient, while not being actively moved by a clinician (e.g. physician, surgeon).

Figure 9:
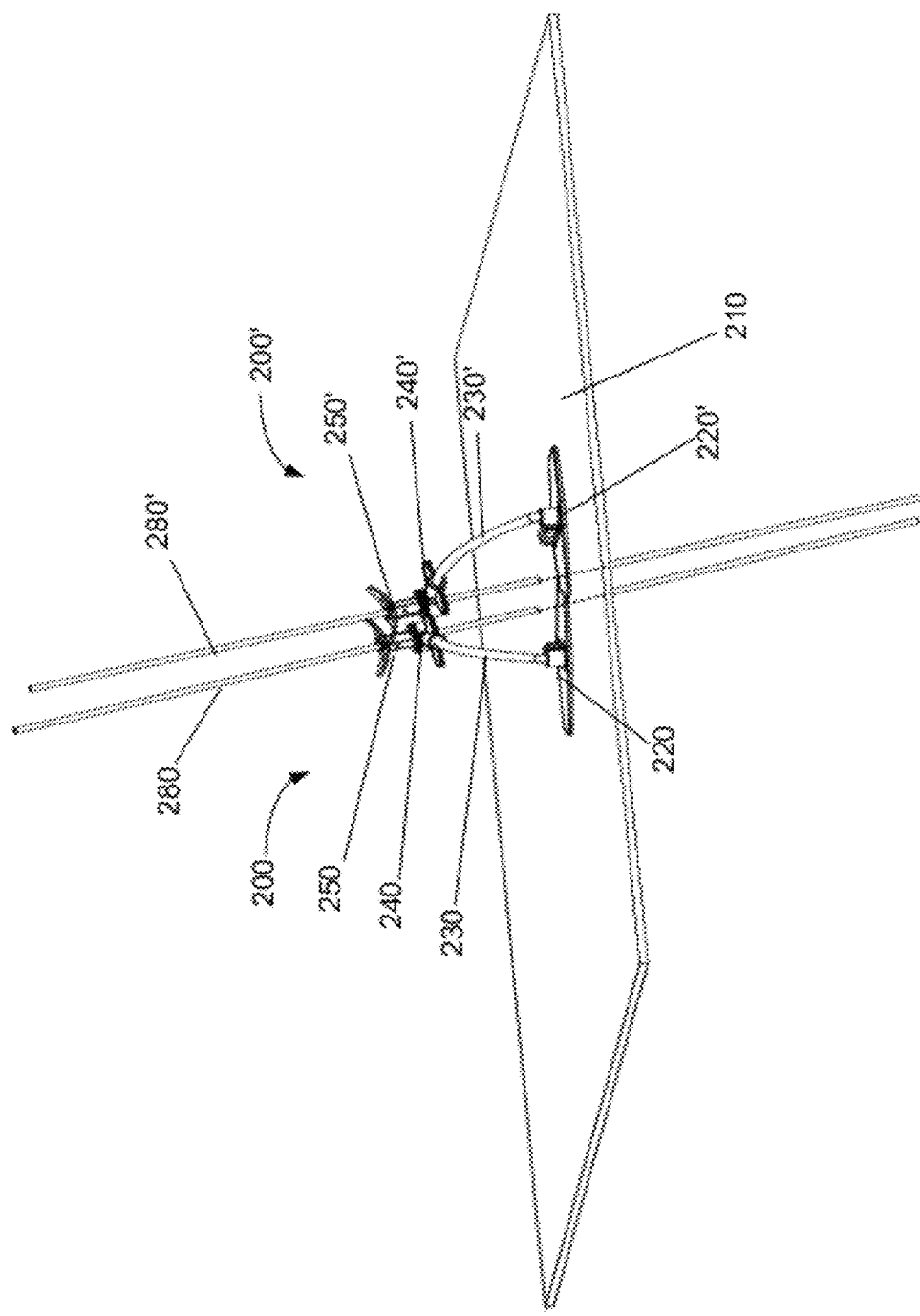
FIG. 9 illustrates the use of two of the stabilization devices of FIG. 2 coupled to a schematic illustration of a patient's skin and an interventional tool coupled to each of the stabilization devices and inserted through the patient's skin.
Figure 10:
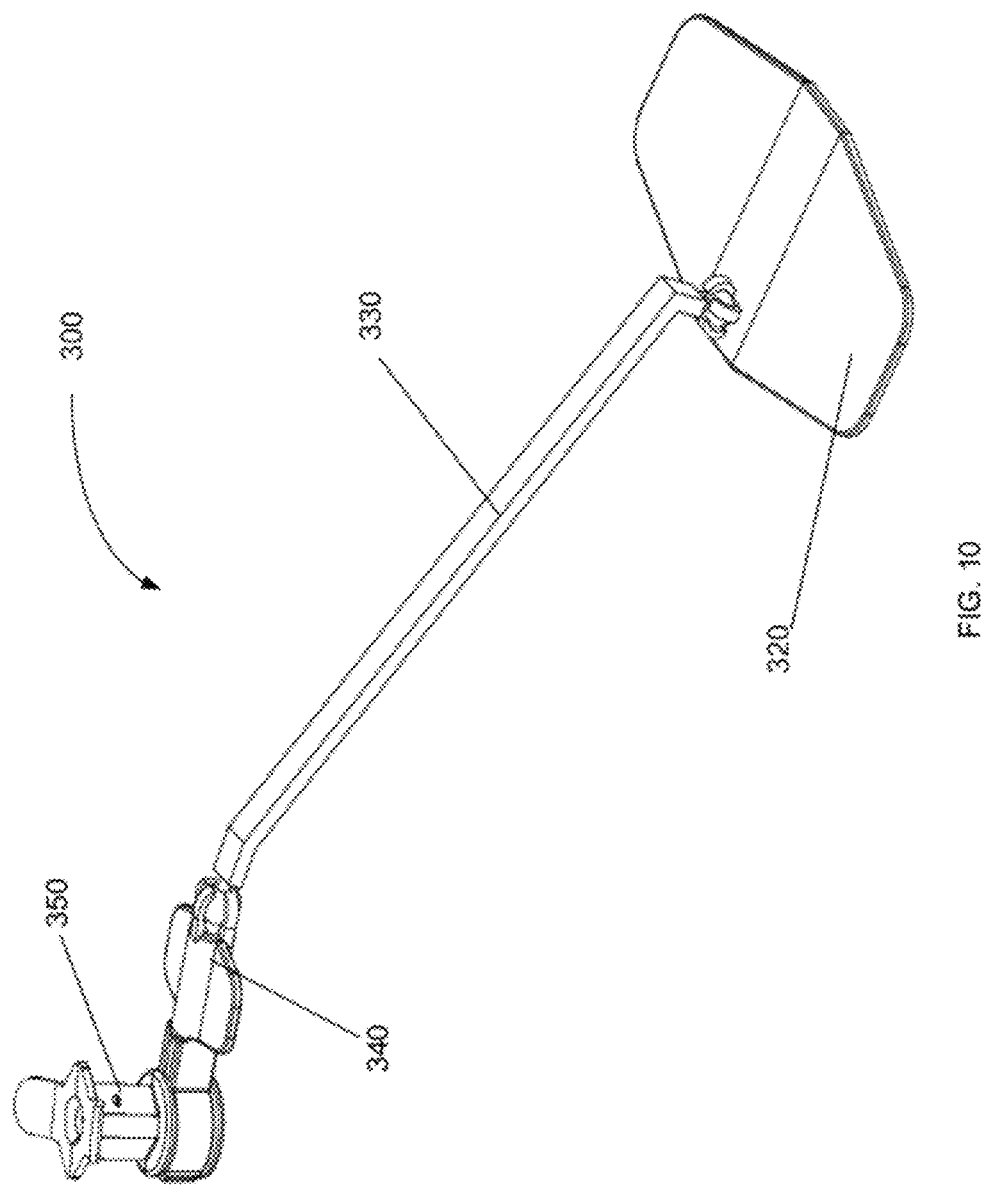
FIG. 10 is a side perspective view of a stabilization device, according to another embodiment.
Figure 11:
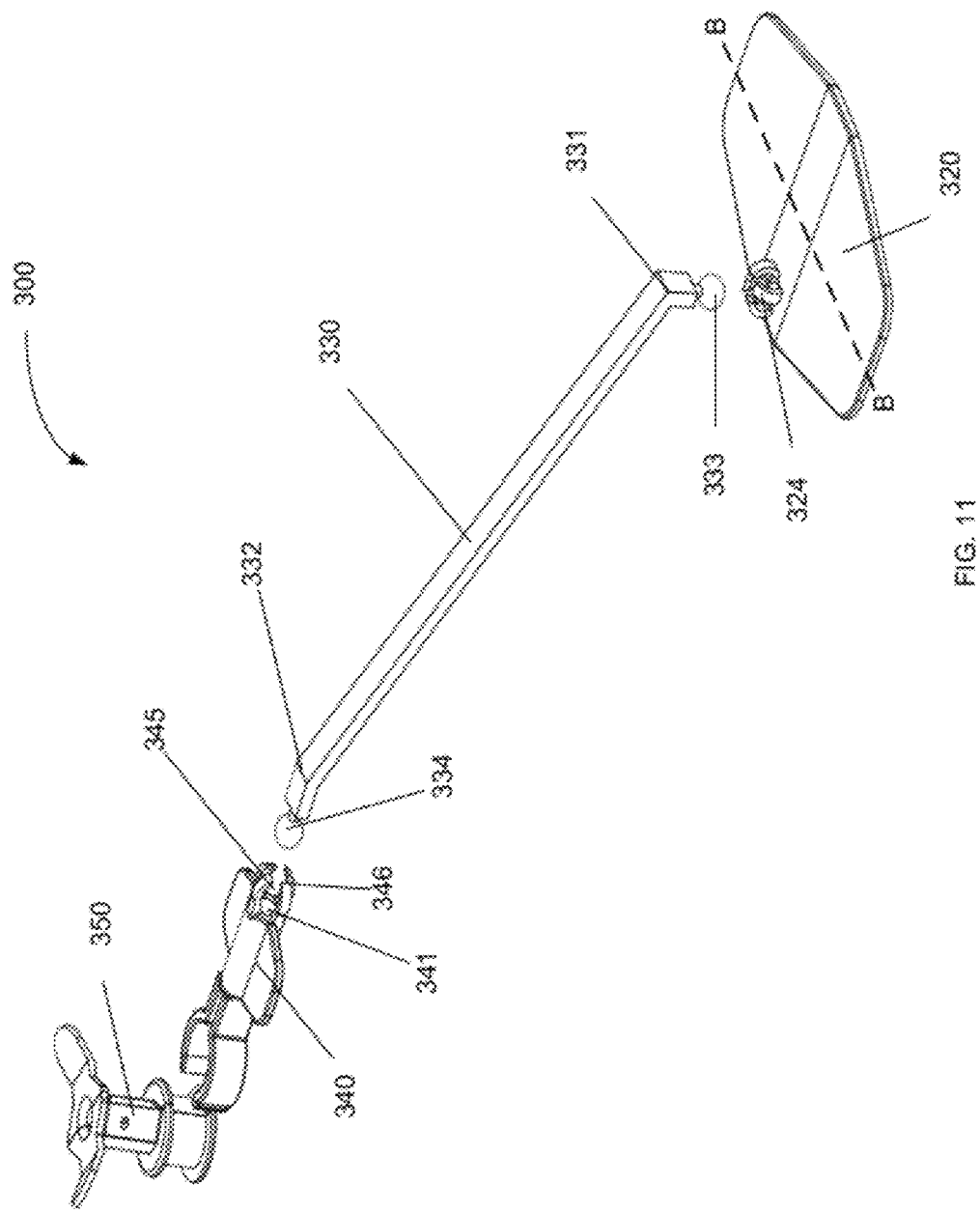
FIG. 11 is an exploded side perspective view of the stabilization device of FIG. 10.

Multiple stabilization devices 200 can also be used simultaneously to stabilize multiple interventional tools 280 during an interventional procedure. For example, two or more stabilization devices 200 can be disposed on a patient in close proximity to each other (shown in FIG. 9), with only minimal or no interference between the bases of the stabilization devices. As shown in FIG. 9, the stabilization device 200 can be used together with a stabilization device 200'. In this example, the stabilization device 200' is configured the same as the stabilization device 200 and includes a base 220', a support member 230', a clamping member 240' and a holder member 250'. The base 220 and the base 220' may in some circumstances have a portion that overlaps one another, without causing interference between the support portions 230, 230', the clamping members 240, 240' and the holder portions 250, 250'. Thus, multiple interventional tools 280 and 280' can be used to treat a target treatment area (e.g., a tumor) within the patient. Although in this example, two stabilization devices having the same configuration are shown and described, it should be understood that multiple stabilization devices can be used having different configurations as described herein.

FIGS. 10-13 illustrate a stabilization device 300 according to another embodiment. The stabilization device 300 includes a base 320, a support member 330, a clamp member 340, and a holder member 350. The stabilizing device 300 can be used to provide support (i.e., stabilization) to an interventional tool (not shown in FIGS. 10-13) as described above for previous embodiments. The base 320 of the stabilization device 300 can be releasably coupled to a patient's skin (not shown in FIG. 10-13), using any suitable method described above (e.g., adhesive or suction). As with the base 220, the base 320 can be any suitable shape and/or size, such as, for example, substantially octagonal, circular, square, elliptical or oblong and can be configured such that the footprint of the base is minimized reducing interference with other devices (e.g. a second stabilization device) and/or operators (e.g., surgeons).

Figure 12:
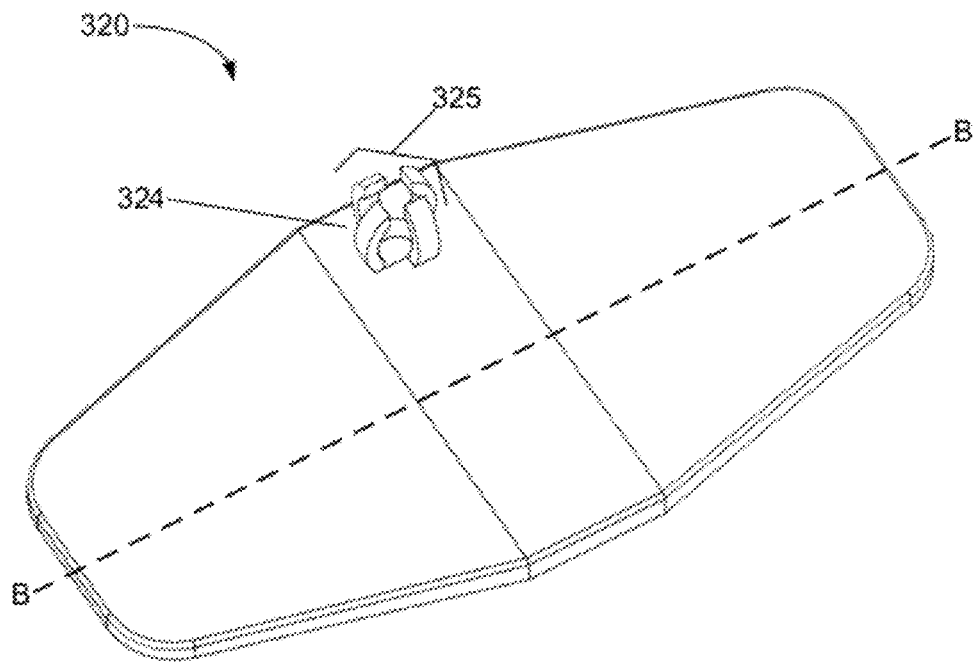
FIG. 12 is an enlarged perspective view of a base of the stabilization device of FIG. 10.

In this embodiment, the base 320 includes a socket protrusion 324 (see, e.g., FIGS. 11 and 12) that can be used to pivotally couple the support member 330 thereto. More specifically, the socket protrusion 324 can include multiple curved fingers 325 (as shown, for example, in FIG. 12), which can be used to couple a first ball member 333 of the support member 330 to the base 320. Similarly stated, the base 320 and the support member 330 couple to form a ball and socket style fitting. The first ball member 333 can be inserted (i.e., pushed) through an opening defined by the multiple curved fingers 325 such that the multiple curved fingers 325 flex or spread apart sufficiently to accept the first ball member 333 therein. Once fully inserted, the socket protrusion 324 provides a pivotal coupling of the support member 330 to the base 320 such that the support member 330 can pivot and/or rotate relative to the base 320. While the socket protrusion 324 includes four curved fingers 325, in other embodiments, the socket protrusion 324 can include more or less fingers 325. Alternatively, the socket protrusion 324 can include multiple curved fingers 325 that are not uniform, thereby accepting the support member 333 in a particular configuration and thus, tailoring the range of motion in a desired fashion. Furthermore, the socket protrusion 324 can be disposed at any suitable position on the base 320, for example, the center of the base 320 or along a longitudinal axis B, as shown in FIG. 12.

The support member 330 includes a first end portion 331, and a second end portion 332. The first end portion 331 includes or is coupled to the first ball member 333, shown in FIG. 11. When the first ball member 333 is coupled to the socket protrusion 324, the support member 330 extends from the base 320 at an angle transverse to the longitudinal axis B defined by the base 320, as shown, for example, in FIG. 10. Thus, the first end portion 331 can be disposed adjacent the base 320 and the second end portion 332 can extend at a desired angle relative to the base 320. The arrangement of the ball and socket coupling allows the angle formed between the support member 330 and the base 320 to be adjustable (i.e., not fixed) and, as such, can be disposed at different positions through a range of positions. In some embodiments, the support member 320 can be substantially rigid such that the movement of the second portion 332 is a result of the first ball member 333 moving within the socket protrusion 324. In some embodiments, the support member 330 can be flexible. Although shown in FIGS. 10 and 11 as substantially square, the support member 330 can be any suitable shape, for example, in some embodiments the support member 330 can be cylindrical, rectangular, oblong, pentagonal, etc.

The second end portion 332 of the support member 330 includes a second ball member 334 that can be used to pivotally couple the support member 330 to a first end portion 341 of the clamping member 340. The first end portion 341 of the clamping member 340 includes a socket protrusion 345 the can extend axially from the first end portion 341 and can receive the second ball protrusion 334 of the support member 330 (see, e.g., FIG. 11). The socket protrusion 345 includes fingers 346 that can be configured similar to or the same as fingers 324 on the base 320. The use of the ball and socket coupling allows the angle created between the support member 330 and the clamping member 340 to be adjustable (i.e., not fixed) and, as such, can be disposed at different positions through a range of positions. While shown in FIGS. 10-13 as extending axially from the first end 341, in some embodiments, the socket protrusion 345 of the clamping member 340 can be disposed at any suitable position on the clamping member 340. For example, the socket protrusion 345 could be disposed at the middle of the clamping member 340 and can extend in a substantially downward direction.

The socket protrusion 324 of the base 320 and the socket protrusion 345 of the clamping member 340 can be any suitable configuration and, in some embodiments, can be dissimilar. For example, the socket protrusion 324 of the base 320 can be of a larger size and/or have a different configuration than the socket protrusion 345 of the clamping member 340. In some embodiments, the ball and socket joint can be replaced by a different coupling method, for example, a universal joint and/or the like.

Figure 13:
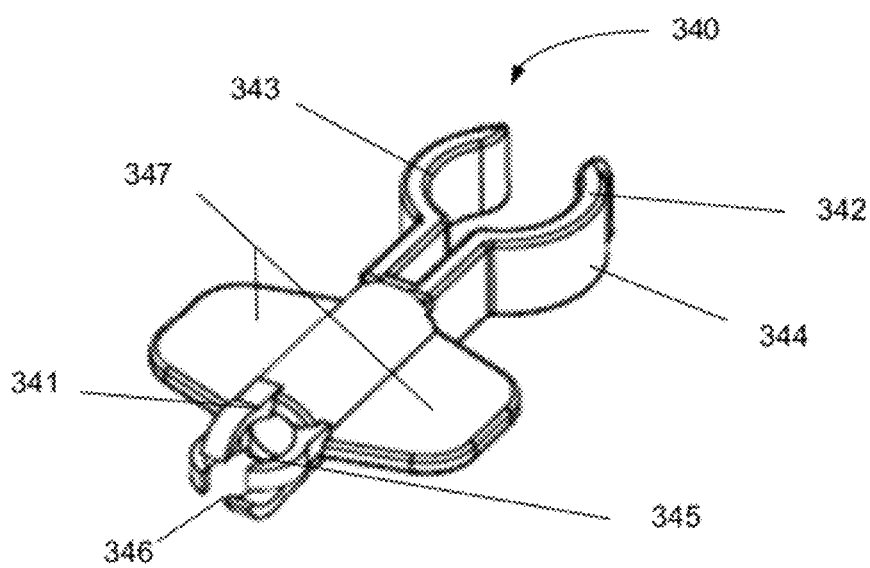
FIG. 13 is an enlarged perspective view of a clamp member of the stabilization device of FIG. 10.

As shown in FIG. 13, the clamping member 340, also includes a second end portion 342, and a pair of wings 347. The wings 347 extend laterally from the centerline of the clamping member 340 and can be used to pivot the clamping member 340 about the second ball member 334 in a similar manner as described above for clamping member 240. For example, a clinician (e.g., a physician) can grasp the wings 347 and pivot the clamping member 340 with respect to the support member 330. The second end portion 342 includes a first clamping arm 343 and a second clamping arm 344. The first clamping arm 343 and the second clamping arm 344 can be used to couple to the holder member 350, in a similar or same manner as described in the previous stabilization device 200. The holder member 350 includes a first end portion 351 and a second end portion 352 and defines an opening 353 therethrough. The opening 353 is configured to receive an interventional tool (not shown in FIGS. 10-13). The holder member 350, shown in FIGS. 10 and 11, functions and is configured similarly to the holder member 250 described in the previous stabilization device 200, and as such, is not described here in depth.

The stabilization device 300 can be used to support or stabilize the position of the interventional tool (not shown in FIGS. 10-13) as described for previous embodiments. With the base 320 of the stabilization device 300 coupled to the skin of the patient, the stabilization device 300 can move with the patient though any potential motion (i.e., breathing or relaxation of muscles). This arrangement allows the interventional tool to maintain the desired angle and position relative to the patient, while not being actively moved by a clinician (e.g. physician, surgeon). Multiple stabilization devices 300 can be used simultaneously in close proximity, allowing for the use of two or more interventional devices during an interventional procedure as previously described.

Figure 16:
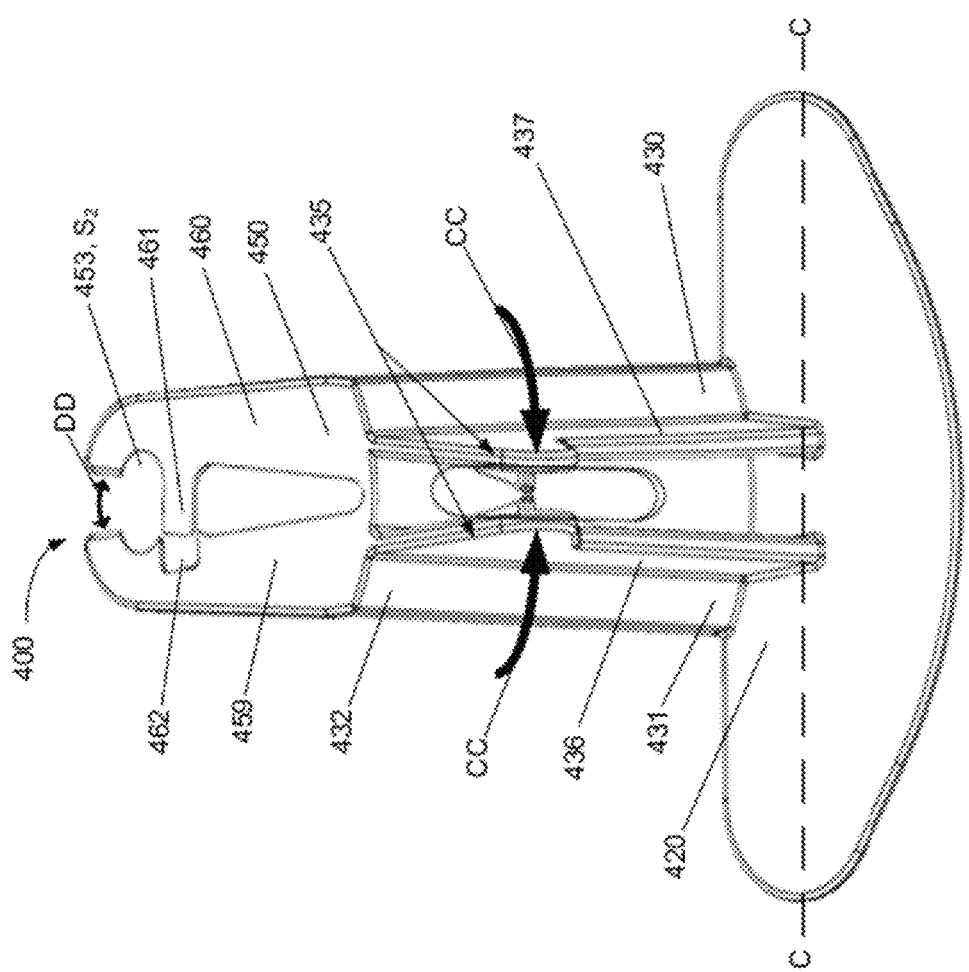
FIG. 16 is a rear view of the stabilization device of FIG. 14, shown with the holder portion in a second configuration.

FIGS. 14-16 illustrate a stabilization device 400 according to another embodiment. The stabilization device 400 includes a base 420, a support portion 430, and a holder portion 450. The stabilizing device 400 can be used to provide support (i.e., stabilization) to an interventional tool (not shown in FIGS. 14-16) in a similar manner as described above for previous embodiments. The base 420 of the stabilization device 400 can be releasably coupled to a patient's skin (not shown in FIG. 14-16), using any suitable method described above (e.g., adhesive or suction). For example, a bottom surface of the base 420 can include an adhesive that can allow the stabilization device 400 to be releasably coupled to the patient's skin. As with previous embodiments, the base 420 can be any suitable shape or size. For example, in some embodiments, the base 420 can be substantially circular, square, or oblong and can be configured such that the footprint of the base is minimized reducing interference with other devices (e.g. a second stabilization device) and/or clinicians (e.g., physicians).

In this embodiment, the support portion 430 of the stabilization device 400 is formed monolithically and/or integrally with the base 420. The support portion 430 extends from the base 420 at an angle transverse to a longitudinal axis C defined by the base 420, as shown, for example, in FIG. 14. For example, the support portion 420 includes a first end portion 431 and a second end portion 432. The first end portion 431 is disposed adjacent the base 420 and the second end portion 432 can extend away from the base 420 at an angle relative to the base 420. The holder portion 450 can extend from the second end portion 432 in a first direction AA, as shown in FIG. 14, and can be monolithically formed with the support portion 430. The support portion 430 includes a grip member 435 that can extend in a second direction BB, substantially opposite the first direction AA, from the support portion 430.

The grip portion 435 includes a first rib member 436 and a second rib member 437 each extending from the support portion 430 in the second direction BB. The grip member 435 can move between a first configuration and a second configuration, such that the holder portion 450 is moved between a first configuration and a second configuration as described in more detail below. Specifically, the first rib member 436 and the second rib member 437 can each be moved between a first configuration (as shown, for example, in FIG. 15), in which the first rib member 436 and the second rib member 437 are substantially parallel to each other, and a second configuration, in which the first rib member 436 and the second rib member 437 are pivoted relative to the support portion 430 as shown in FIG. 16. In use, the clinician (e.g., physician) can apply a squeezing pressure to the first rib member 436 and the second rib member 437, as shown in FIG. 16 by arrow CC, to move the grip member 435 from its first configuration to its second configuration.

The holder portion 450 includes a first holder arm 459 and a second holder arm 460 that collectively define an opening 453. The opening 453, as shown in FIG. 15, can receive at least a portion of the interventional tool therethrough (not shown in FIGS. 14-16). When the grip member 435 is in its first configuration (e.g., the first rib member 436 and the second rib member 437 are substantially parallel to each other) the holder portion 450 is in its first configuration and the opening 453 defined by the first holder arm 459 and the second holder arm 460 has a first size S₁. When the opening 453 has the first size S₁, an interventional tool (not shown) can be received therethrough and maintained within the opening 453. When the grip member 435 is in its second configuration (e.g., the first rib member 436 and the second rib member 437 are pivoted relative to the support portion 430) the holder portion 450 will be in its second configuration and the opening 453 defined by the first holder arm 459 and the second holder arm 460 will have a second size S₂ different than the first size.

As described above, the first rib member 436 and the second rib member 437 are substantially parallel when the grip member 435 is in its first configuration and the first holder arm 459 and the second holder arm 460 are substantially closed as shown, for example, in FIG. 14. In this configuration, an interventional tool (not shown in FIGS. 14-16) can be disposed within the opening 453, but may not be permitted to be moved out of the opening 453 in a lateral direction. When the grip member 435 is moved to its second configuration (e.g., the first rib member 436 and the second rib member 437 are pivoted or squeezed, the first holder arm 459 and the second holder arm 460 are spread apart (as indicated by the arrow DD in FIG. 16) a distance sufficient to allow the interventional tool to be laterally moved out of the opening 453.

The second holder arm 460 includes a tab 461 that extends laterally from the second holder arm 460. The first holder arm 459 includes a receiving portion 462 that can receive the tab 461 when the holder portion 450 is in its first configuration, as shown, for example in FIG. 15. The tab 461 and receiving portion 462 can be used to align the first holder arm 459 and the second holder arm 460.

As with previous embodiments, the stabilization device 400 can be used to support or stabilize the position of the interventional tool (not shown in FIGS. 14-16) during an image-guided interventional procedure. For example, the base 420 of the stabilization device 400 can be coupled to the skin of the patient, and an interventional tool can be placed through the opening 453. The stabilization device 400 can stabilize and support the interventional tool as the clinician uses the interventional tool to treat a target tissue in the patient. Although not shown, multiple stabilization devices 400 can be used simultaneously in close proximity, allowing for the use of two or more interventional devices to be used during an interventional procedure.

Figure 17:
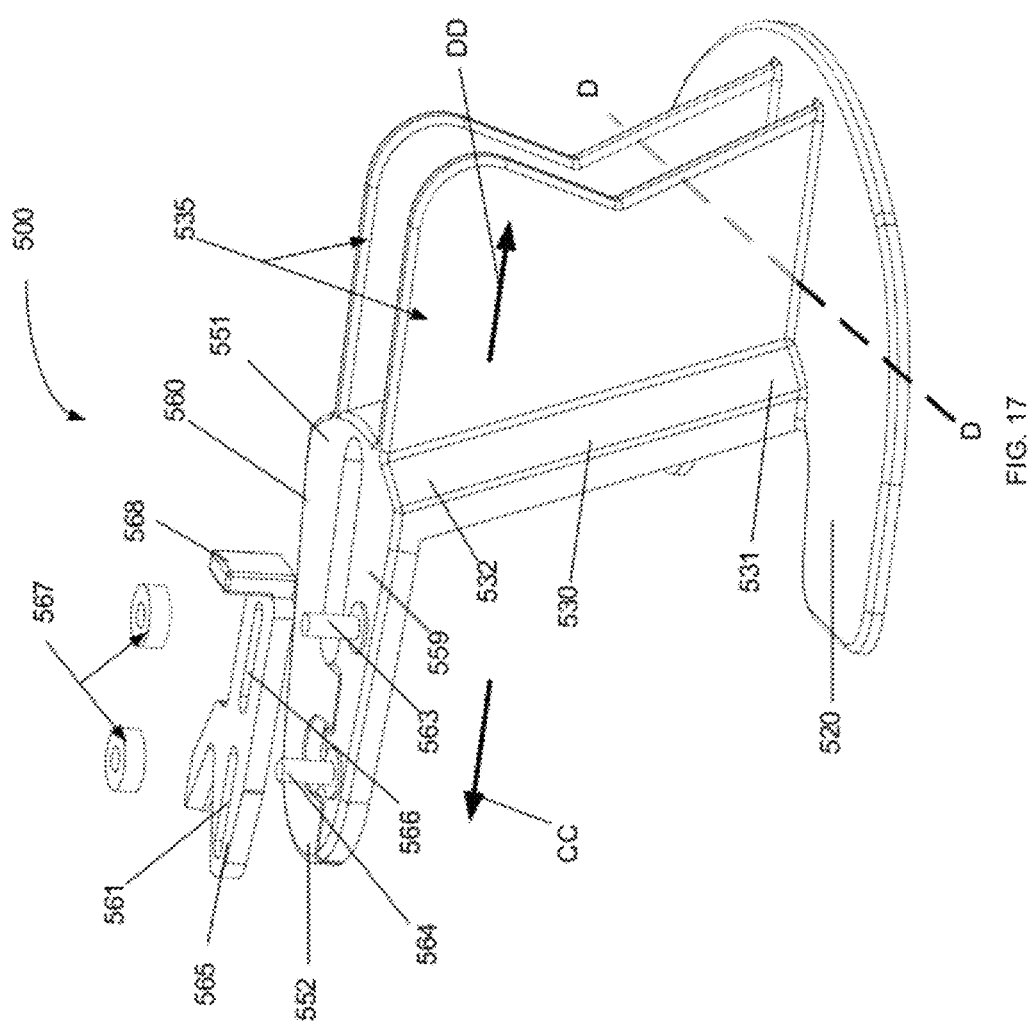
FIG. 17 is an exploded side perspective view of a stabilization device, according to another embodiment.
Figure 18:
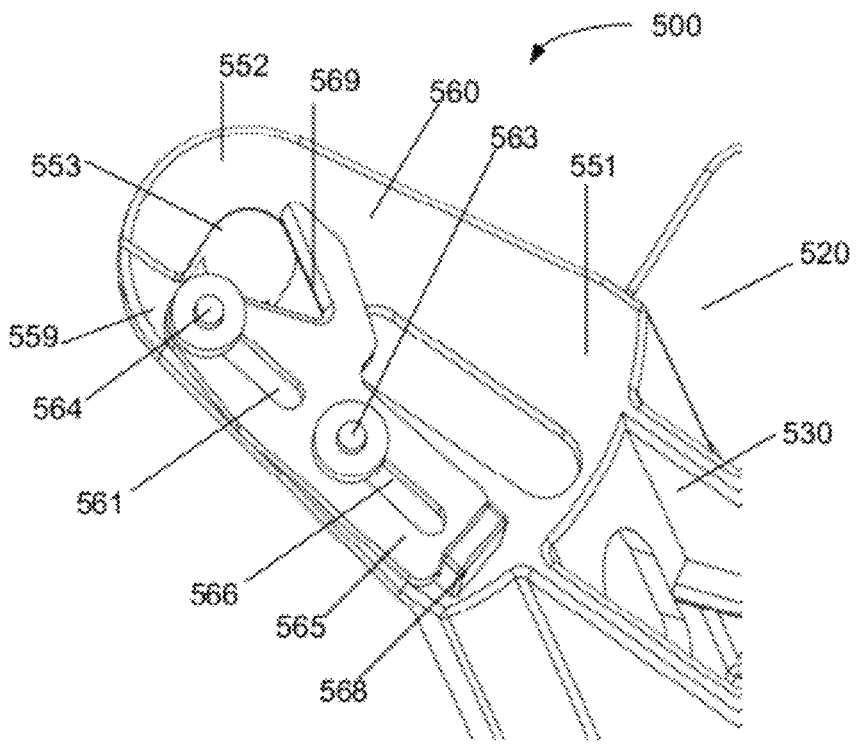
FIG. 18 is a top perspective view of a portion of the stabilization device of FIG. 17, shown in a first configuration.
Figure 19:
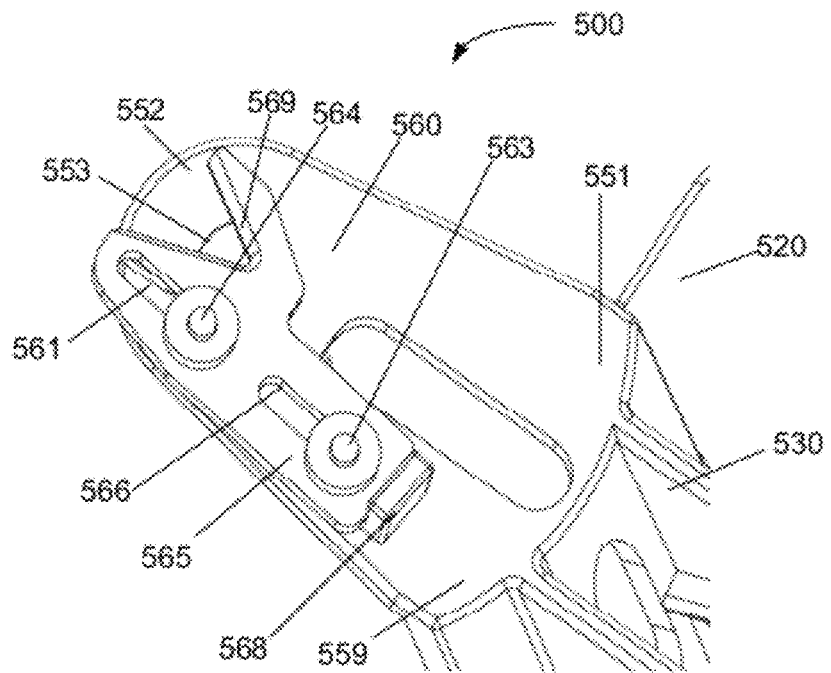
FIG. 19 is a top perspective view of a portion of the stabilization device of FIG. 17, shown in a second configuration.

FIGS. 17-19 illustrate a stabilization device 500 according to another embodiment. The stabilization device 500 includes a base 520, a support portion 530, and a holder portion 550. As with previous embodiments, the stabilizing device 500 can be used to provide support (i.e., stabilization) to an interventional tool (not shown in FIGS. 17-19) during an image-guided interventional procedure. The base 520 of the stabilization device 500 can be releasably coupled to a patient's skin (not shown in FIG. 17-19), using any suitable method described above (e.g., adhesive or suction). The base 520, the support portion 530 and the holder portion 550 can be configured the same or similar as the stabilization device 400.

For example, the support portion 530 can be formed monolithically and/or integrally with the base 520. The support portion 530 extends from the base 520 at an angle transverse to a longitudinal axis D defined by the base 520, as shown in FIG. 17. The holder portion 550 is monolithically formed with the support portion 530 and extends from the support portion 530 in a first direction CC. The support portion 530 includes a grip member 535 that can extend in a second direction DD, substantially opposite the first direction CC, from the support portion 530. The structure and function of the support portion 530, including the grip member 535, are similar to the structure and function of the support portion 430 and are therefore not described in detail herein.

The holder portion 550 includes a first holder arm 559 and a second holder arm 560 that collectively define an opening 553. The opening 553, as shown in FIG. 18, can receive at least a portion of an interventional tool therethrough (not shown in FIG. 17-19). The holder portion 550 can be moved between a first configuration and a second configuration by the grip member 535 in a similar way as described above for the stabilization device 400, and therefore, is not described in detail herein.

In this embodiment, the holder member 550 also includes an adjustment mechanism 565 that can be used to adjust an effective opening through which the interventional tool can extend, as described in more detail below. The first holder arm 559 includes a first pin member 563 and a second pin member 564 that extend from a surface of the first holder arm 559. The adjustment mechanism 565 includes a first track or slot 566 through which the first pin member 563 extends and a second track or slot 561 through which the second pin member 564 extends. A pair of fasteners 567 couple to the first pin member 563 and the second pin member 564 thereby slidably coupling the adjustment mechanism 565 to the holder member 550. The adjustment mechanism 565 includes a gripping portion 568 that can be used to slide the adjustment mechanism 565 between a first configuration, as shown in FIG. 18, and a second configuration, as shown in FIG. 19. For example, a clinician (e.g., physician) can grasp the gripping portion 568 and slide the adjustment mechanism 565 from the first configuration to the second configuration. The adjustment mechanism 565 includes an adjusting portion 569. When the adjustment mechanism 565 is in the first configuration, the adjustment portion 569 is rearward (i.e., closer to the first end 551 of the holder member 550) of the opening 553. Thus, when the adjustment member 565 is in the first configuration, the opening 553 is substantially uncovered by the adjustment portion 569. As the adjustment mechanism 565 is slid from its first configuration towards its second configuration, the adjustment portion 569 at least partially closes or covers the opening 553 effectively reducing the size of the opening 553 through which an interventional tool can be disposed.

In some embodiments, the adjustment mechanism 565 can include one or more springs (not shown) to modify the sliding and or stabilizing characteristics of the adjustment mechanism 565. For example, a spring mechanism can be used to maintain the adjustment mechanism 565 in the second configuration until an additional force, greater than the force exerted by the spring mechanism, is applied. In other embodiments, a latching or catch mechanism can be used to modify the characteristics of the adjustment mechanism 565.

Figure 20:
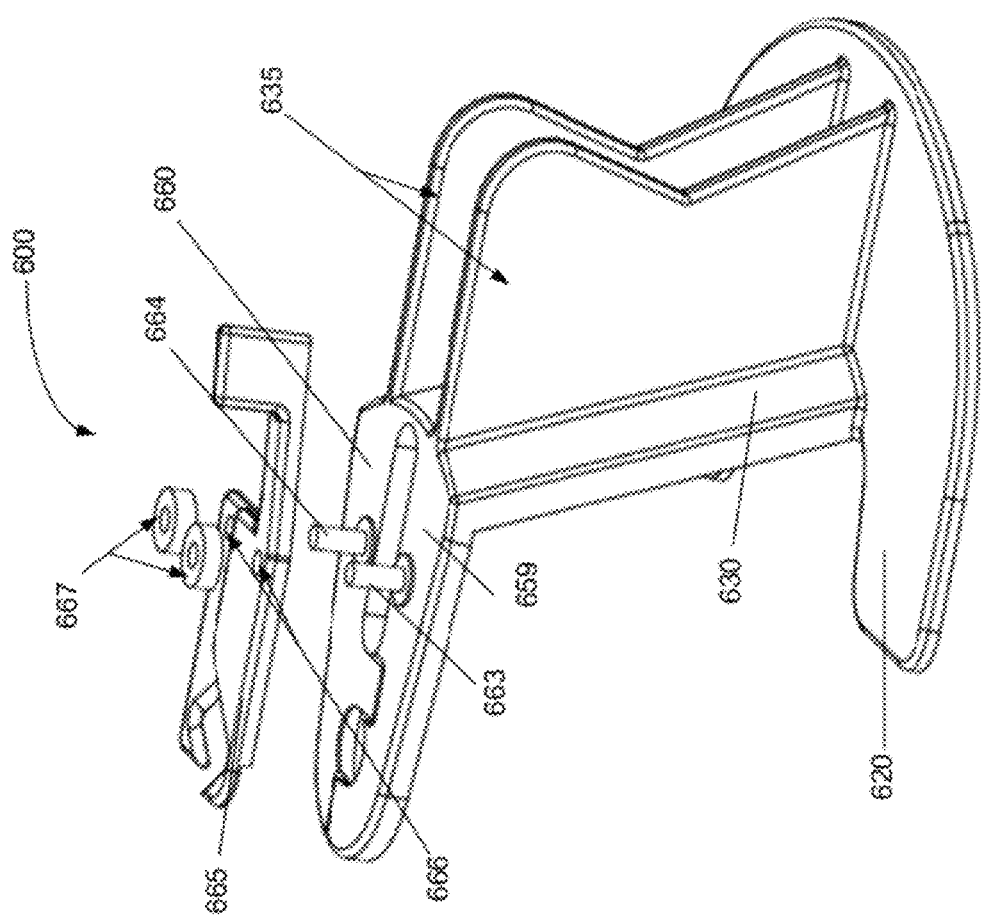
FIG. 20 is an exploded side perspective view of a stabilization device, according to another embodiment.
Figure 21:
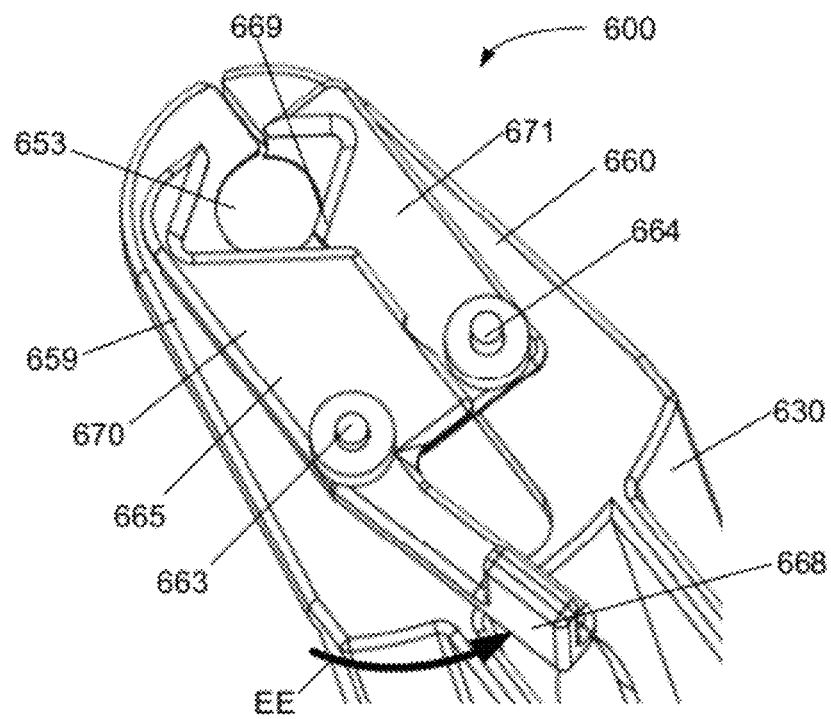
FIG. 21 is a top perspective view of a portion of the stabilization device of FIG. 20, shown in a first configuration.
Figure 22:
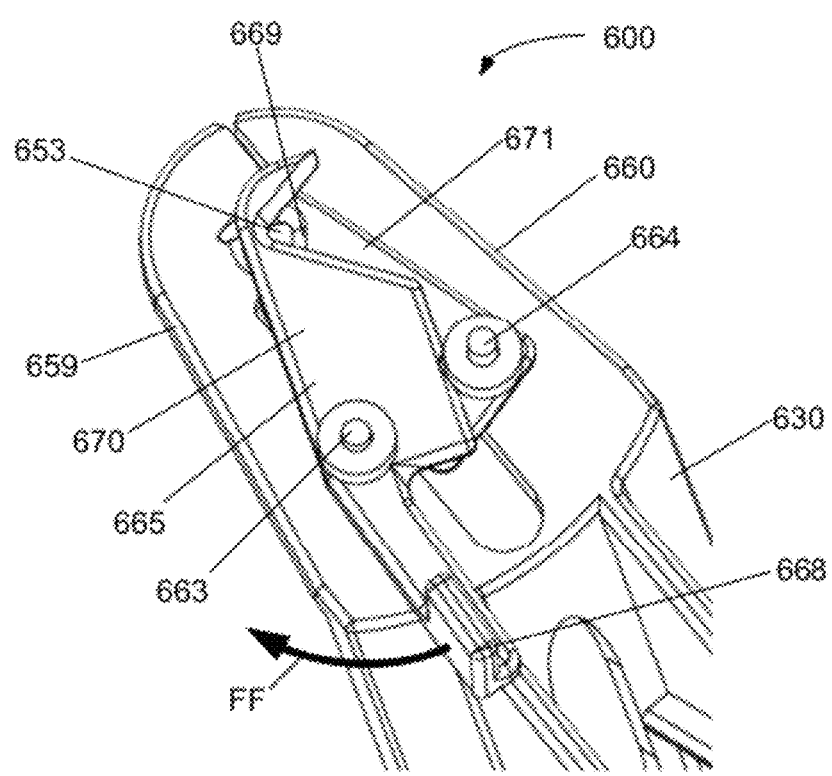
FIG. 22 is a top perspective view of a portion of the stabilization device of FIG. 20, shown in a second configuration.

FIGS. 20-22 illustrate another embodiment of a stabilization device 600 that includes an adjustment mechanism. The stabilization device 600 includes a base 620, a support portion 630, and a holder portion 650. The stabilizing device 600 can be used to provide support (i.e., stabilization) to an interventional tool (not shown in FIGS. 20-22) as described above for previous embodiments. The base 620 of the stabilization device 600 can be releasably coupled to a patient's skin (not shown in FIG. 20-22), using any suitable method described above (e.g., adhesive or suction).

Similar to the stabilization device 400, the support portion 630 of the stabilization device 600 includes a grip member 635. The structure and function of the support portion 630 (including the grip member 635) are similar to the structure and function of the support portion 430, and therefore are not described in detail herein. The holder portion 650 includes a first holder arm 659 and a second holder arm 660 that collectively define an opening 653. The opening 653, as shown in FIG. 21, can receive at least a portion of an interventional tool therethrough (not shown in FIG. 20-22). The function of the holder portion 650 is similar to the function of the holder portion 450 defined by the stabilization device 400. For example, the clinician (e.g., physician) can apply pressure to the grip member 635 and subsequently move the holder portion 650 to a second configuration (i.e., substantially open). Thus, the function and method is similar to the function and method of the stabilization device 400 and is not described in detail for this embodiment.

In this embodiment, the holder portion 650 includes a first pin member 663 and a second pin member 664 extending from the first holder arm 659 and the second holder arm 660, respectively. The adjustment mechanism 665 includes a first aperture 666 and a second aperture 661 that can receive the first pin member 663 and the second elongate 664, respectively. A pair of fasteners 667 can pivotally couple the adjustment mechanism 665 to the holder portion 650 (e.g., the adjustment mechanism 665 can be disposed on a top surface of the holder arms 659 and 660, as shown, in FIGS. 21 and 22). More specifically, the adjustment mechanism 665 can have a first adjustment arm 670 and a second adjustment arm 671 that can pivot about the first pin member 663 and the second pin member 664, respectively. The adjustment mechanism 665 includes a gripping portion 668 that can be used to move the adjustment mechanism 665 between a first configuration, as shown in FIG. 21, and a second configuration, as shown in FIG. 22. For example, a clinician (e.g., physician) can move the gripping portion 668 in a direction of arrow EE (as shown in FIG. 21) to place the adjustment mechanism 665 in its first configuration, and move the gripping portion in a direction of arrow FF (as shown in FIG. 22) to move the adjustment mechanism 665 to its second configuration. The adjustment mechanism 665 includes an adjusting portion 669 collectively defined by the first adjustment arm 670 and the second adjustment arm 671. When the adjustment mechanism 665 is in its first configuration, the adjustment portion 669 is in a substantially open position (i.e., the first adjustment arm 670 and the second adjustment arm 671 are positioned such as to not obstruct the opening 653). As the adjustment mechanism 665 is moved from its first configuration towards its second configuration, the adjustment portion 669 reduces the effective size of the opening 653 through which an interventional tool can be disposed. More specifically, the gripping portion 668 can be used to pivot the first adjustment arm 670 toward the second adjustment arm 671 and vice versa. As such, the adjustment portion 669 overlaps (e.g., covers, blocks, and/or reduces) the opening 653. As described above for stabilization device 500, in some embodiments, the adjustment mechanism 665 can include a spring or springs to modify the pivoting and/or stabilizing characteristics of the adjustment mechanism 665 or a latching or catch mechanism can be used to maintain the adjustment mechanism 665 in the second configuration.

Figure 23:
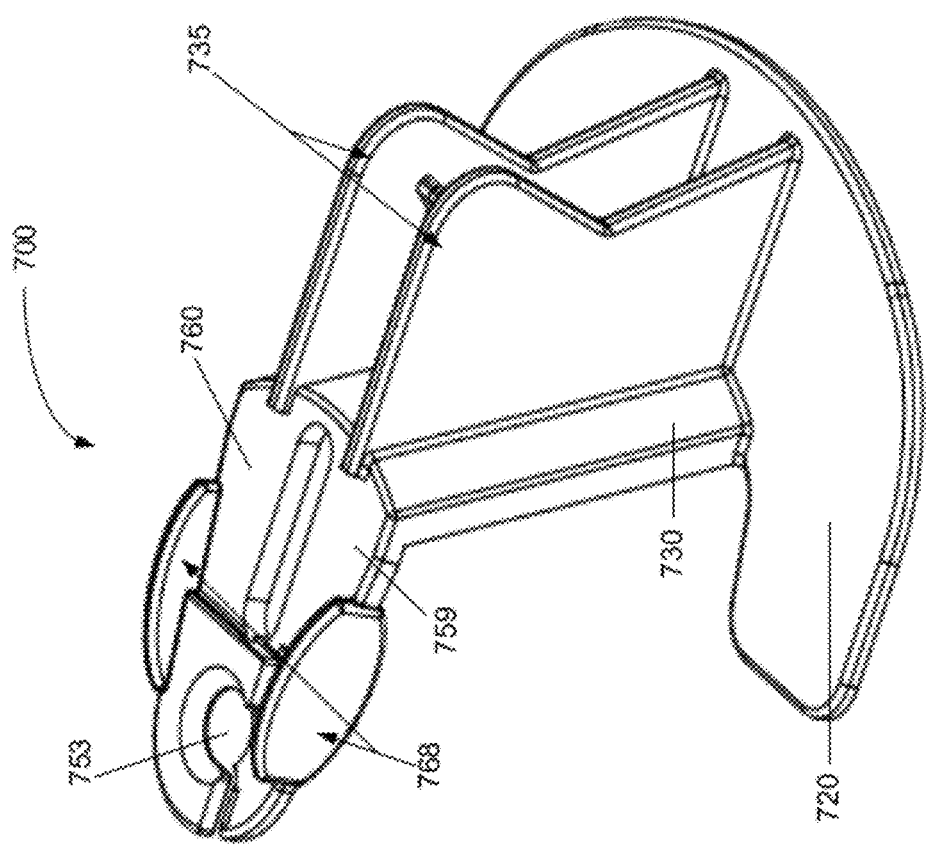
FIG. 23 is a side perspective view of a stabilization device, according to another embodiment.
Figure 24:
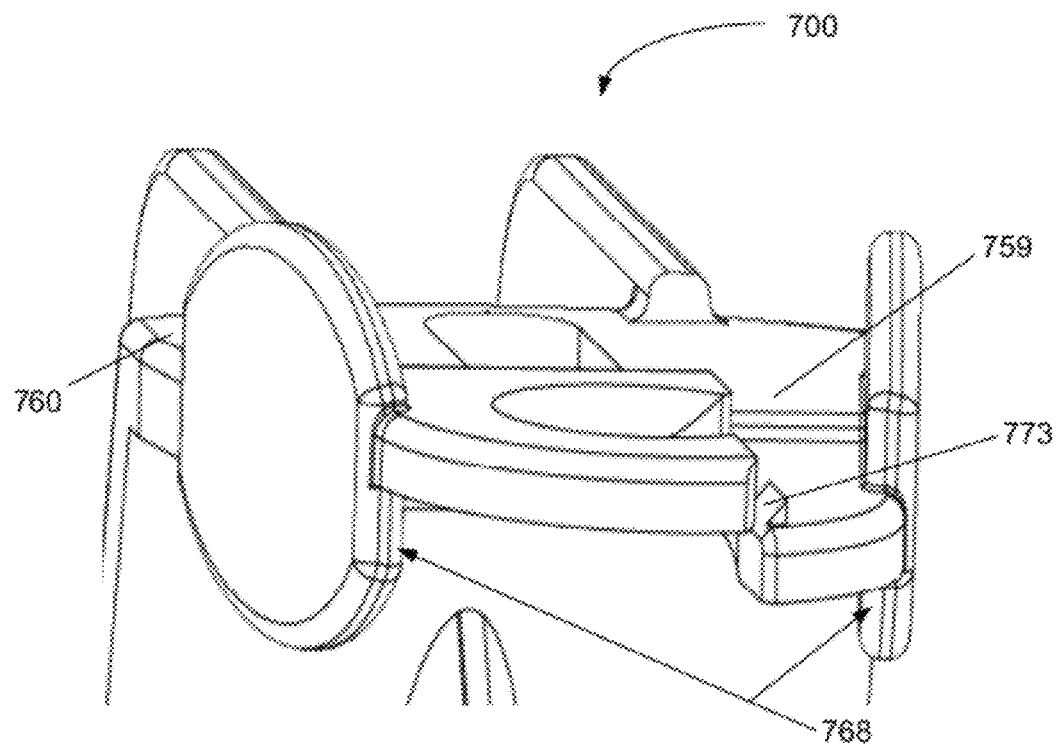
FIG. 24 is a front perspective view of a portion of the stabilization device of FIG. 23.
Figure 25:
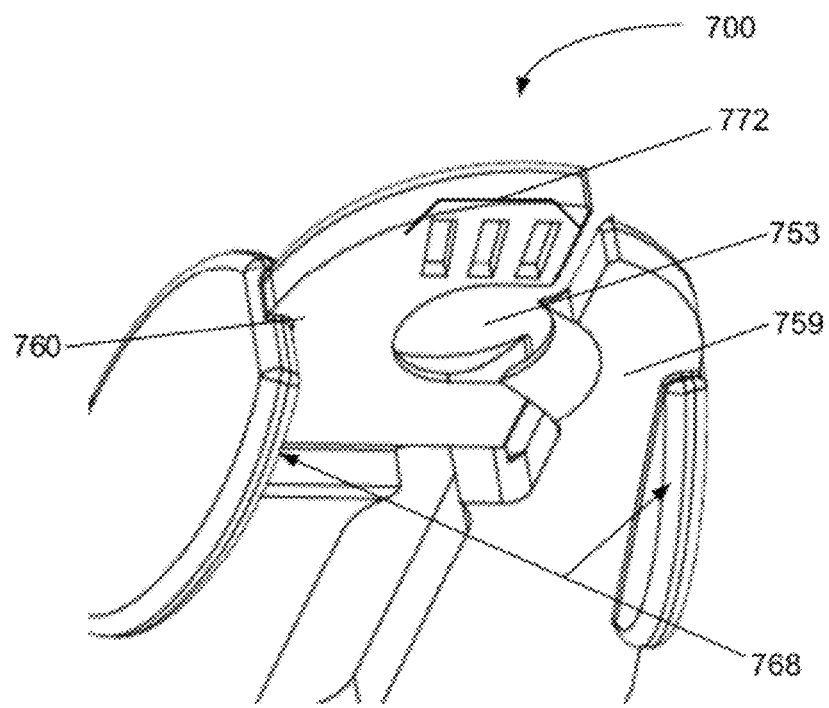
FIG. 25 is a bottom perspective view of a portion of the stabilization device of FIG. 23.

FIGS. 23-25 illustrate a stabilization device 700 according to another embodiment. In this embodiment, the stabilization device 700 includes a ratcheting adjustment portion. The stabilization device 700 includes a base 720, a support portion 730, and a holder portion 750. The stabilizing device 700 can be used to provide support (i.e., stabilization) to an interventional tool (not shown in FIGS. 23-25) as describe above for previous embodiments. The base 720 of the stabilization device 700 can be releasably coupled to a patient's skin (not shown in FIG. 23-25), using any suitable method described above (e.g., adhesive or suction).

Similar to the stabilization device 400, the support portion 730 of the stabilization device 700 includes a grip member 735. The structure and function of the support portion 730 (including the grip member 735) are similar to the structure and function of the support portion 430 of the stabilization device 400, and therefore are not described in detail herein.

The holder portion 750 includes a first holder arm 759 and a second holder arm 760 that collectively define an opening 753. The opening 753, as shown in FIG. 23, can receive at least a portion of an interventional tool therethrough (not shown in FIG. 23-25) as previously described for other embodiments. The grip member 735 of the stabilization device 700 can be used to move the holder portion 750 between a first configuration in which the holder portion 750 is substantially closed and the opening 753 has a first size, and a second configuration in which the holder portion 750 is at least partially opened and the opening 753 has a second size different than its first size. For example, the clinician (e.g., physician) can apply a squeezing pressure to the grip member 735 to move the holder portion 750 from its first configuration to its second configuration (e.g., the first holder arm 759 and the second holder arm 760 are spread apart). Therefore, in the second configuration, the size of the opening is larger than the size of the opening 753 in the first configuration.

The first holder arm 759 and the second holder arm 760 include a gripping portion 768 that can be used to move the holder portion 750 to a third configuration. The holder portion 750 includes a ratcheting extension 773, as shown in FIG. 24, and a set of ratcheting teeth 772, as shown in FIG. 25. In use, the clinician (e.g., physician) can grasp the gripping portion 768 of the holder member 750 and apply a squeezing pressure, thereby moving the first holder arm 759 and the second holder arm 760 closer together. The ratcheting extension 773 can adjustably couple to the ratcheting teeth 772 such that an increase in squeezing pressure applied to the gripping portion 768 of the holder member 750 results in the ratcheting extension 773 coupling to the next ratcheting tooth 772. As such, the size of the opening 753 can be reduced as desired to provide a desired level of stabilization to the interventional tool disposed therethrough. The grip member 735 can be used to move the holder portion from the third configuration back to the first configuration and subsequently to the second configuration, releasing the interventional tool disposed therethrough.

The gripping portion 768 of the holder member 750, as shown in FIGS. 23-25, includes substantially flat protrusions extending from the top and bottom surfaces of the holder arms 759 and 760. Although shown in FIG. 23-25, as substantially oblong the gripping portion 768 could be any suitable shape. For example, in some embodiments, the gripping portion 768 can be rectangular or circular. Similarly, in some embodiments, the gripping portion 768 can be concave and/or textured increasing ergonomics.

Figure 26:
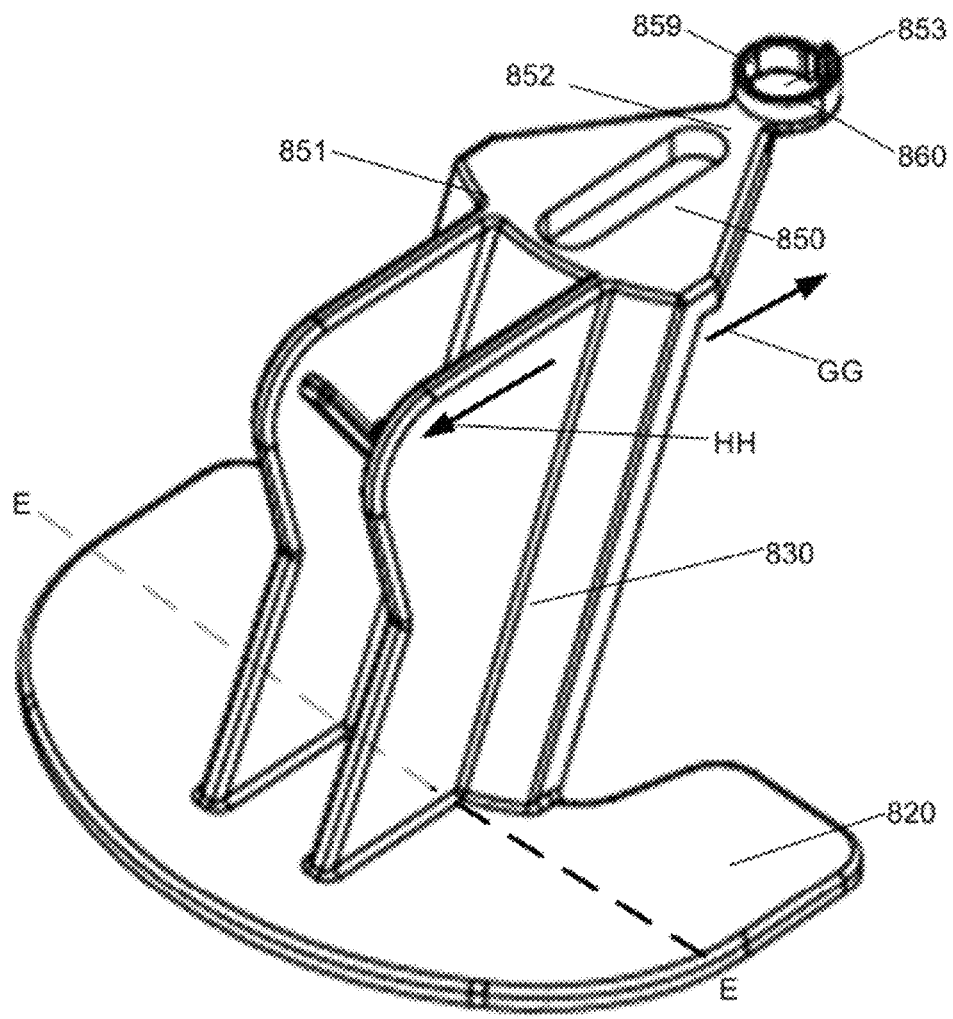
FIG. 26 is a rear perspective view of a stabilization device, according to another embodiment.
Figure 27:
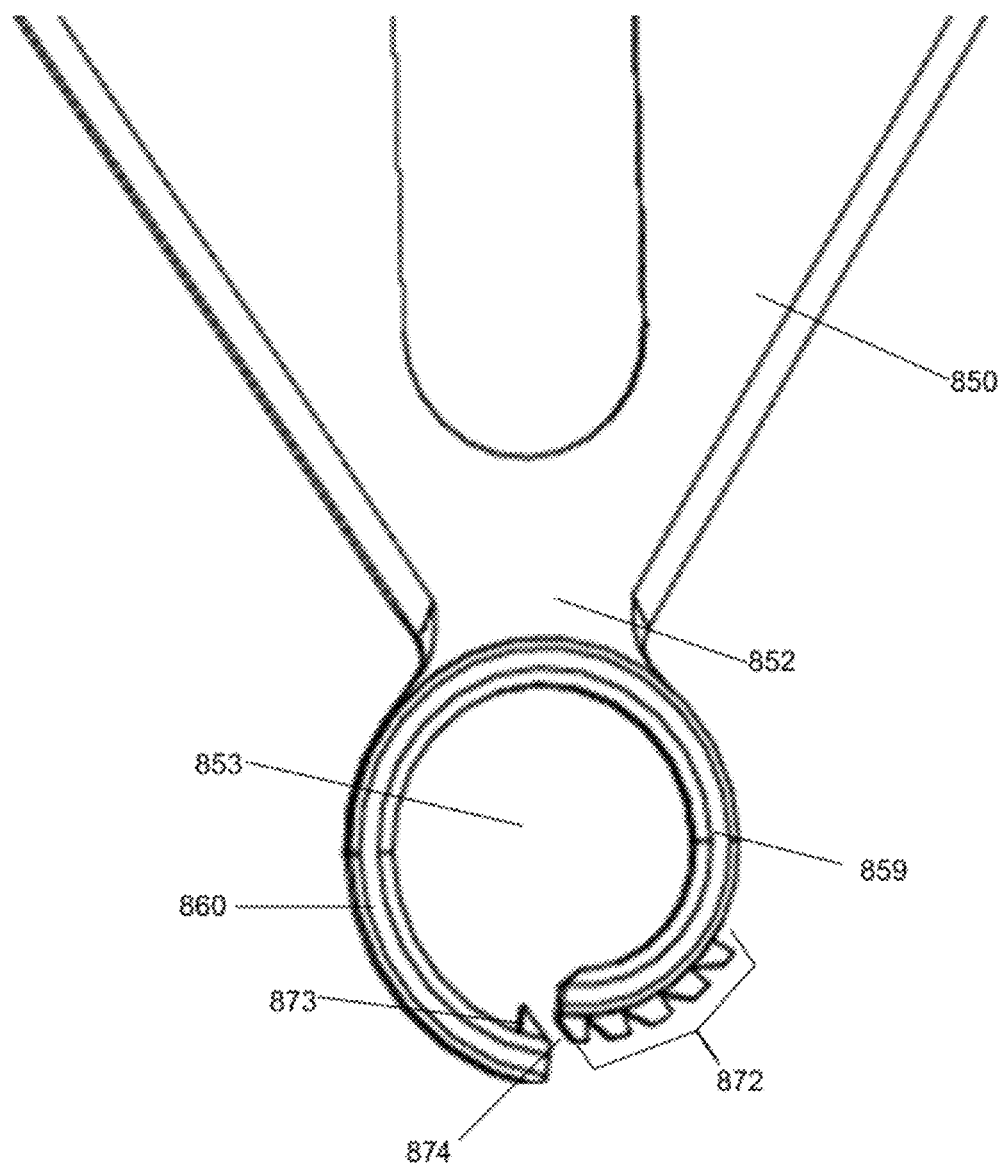
FIG. 27 is a top view of a portion of the stabilization device of FIG. 26.

FIGS. 26 and 27 illustrate a stabilization device 800 according to another embodiment that includes a ratcheting adjustment mechanism. The stabilization device 800 includes a base 820, a support portion 830, and a holder portion 850. The stabilizing device 800 can be used to provide support (i.e., stabilization) to an interventional tool (not shown in FIGS. 26 and 27) as described above for previous embodiments. The base 820 of the stabilization device 800 can be releasably coupled to a patient's skin (not shown in FIGS. 26 and 27), using any suitable method described above (e.g., adhesive or suction).

The support portion 830 of the stabilization device 800 can be formed monolithically and/or integrally with the base 820. The support portion 830 extends from the base 820 at an angle transverse to a longitudinal axis E defined by the base 820, as shown in FIG. 26. For example, the support portion 820 includes a first end portion 831 and a second end portion 832, the first end portion 831 is disposed adjacent the base 820 and the second end portion 832 can extend away from the base 820 at an angle relative to the base 820. The holder portion 850 can extend from the second end portion 832 in a first direction GG, as shown in FIG. 26, and can be monolithically formed with the support portion 830. The support portion 830 includes a grip member 835 that can extend in a second direction HH, substantially opposite the first direction AA, from the support portion 830.

The holder member 850 includes a first end portion 851 and a second end portion 852. The second end portion 852 can include a first holder arm 859 and a second holder arm 860 that collectively define an opening 853. The opening 853 can receive an interventional tool therethrough (not shown in FIGS. 26 and 27) as described for previous embodiments. The first holder arm 859 and the second holder arm 860 are each curved extensions that can be moved between a first configuration, in which the first holder arm 859 and the second holder arm 860 define an opening 874 (as shown in FIG. 27), and a second configuration, in which the first holder arm 859 and the second holder arm 860 are coupled together (e.g., closing the opening 874) as shown in FIG. 26.

The first holder arm 859 includes a set of ratcheting teeth 872 and the second holder arm 860 includes a ratcheting extension 873, as shown, for example, in FIG. 27. The holder portion 850 can be placed in the second configuration by moving the first holder arm 859 and the second holder arm 860 closer together, such that the ratcheting extension 873 interlocks with the ratcheting teeth 872, coupling the first holder arm 859 to the second holder arm 860. For example, the clinician (e.g., physician) can apply a squeezing pressure to the first holder arm 859 and the second holder arm 860. As the pressure is applied, the ratcheting extension 873 contacts the ratcheting teeth 872 such that as more pressure is applied, the ratcheting extension 873 will interlock with a subsequent ratcheting tooth 872 further reducing the size of the opening 853. Thus, when the holder portion 850 is in the second configuration, the holder portion 850 can further be moved or adjusted between multiple different positions varying the size of the opening 853. The ratcheting teeth 872 and the ratcheting extension 873 can maintain the holder portion 850 in the second configuration until a device and/or the clinician remove the ratcheting extension 873 from the ratcheting teeth 872.

FIGS. 28-32 illustrate a stabilization device 900 according to another embodiment. The stabilization device 900 includes a base 920, a support member 930, a clamp member 940, and a holder member 950. The stabilizing device 900 can be used to provide support (i.e., stabilization) to an interventional tool (not shown in FIGS. 28-32) as described above for previous embodiments. The base 920 of the stabilization device 900 can be releasably coupled to a patient's skin (not shown in FIG. 28-32), using any suitable method described above (e.g., adhesive or suction). As with the base 320, the base 920 can be any suitable shape and/or size, such as, for example, substantially octagonal, circular, square, elliptical or oblong and can be configured such that the footprint of the base is minimized reducing interference with other devices (e.g. a second stabilization device) and/or operators (e.g., surgeons).

Figure 29:
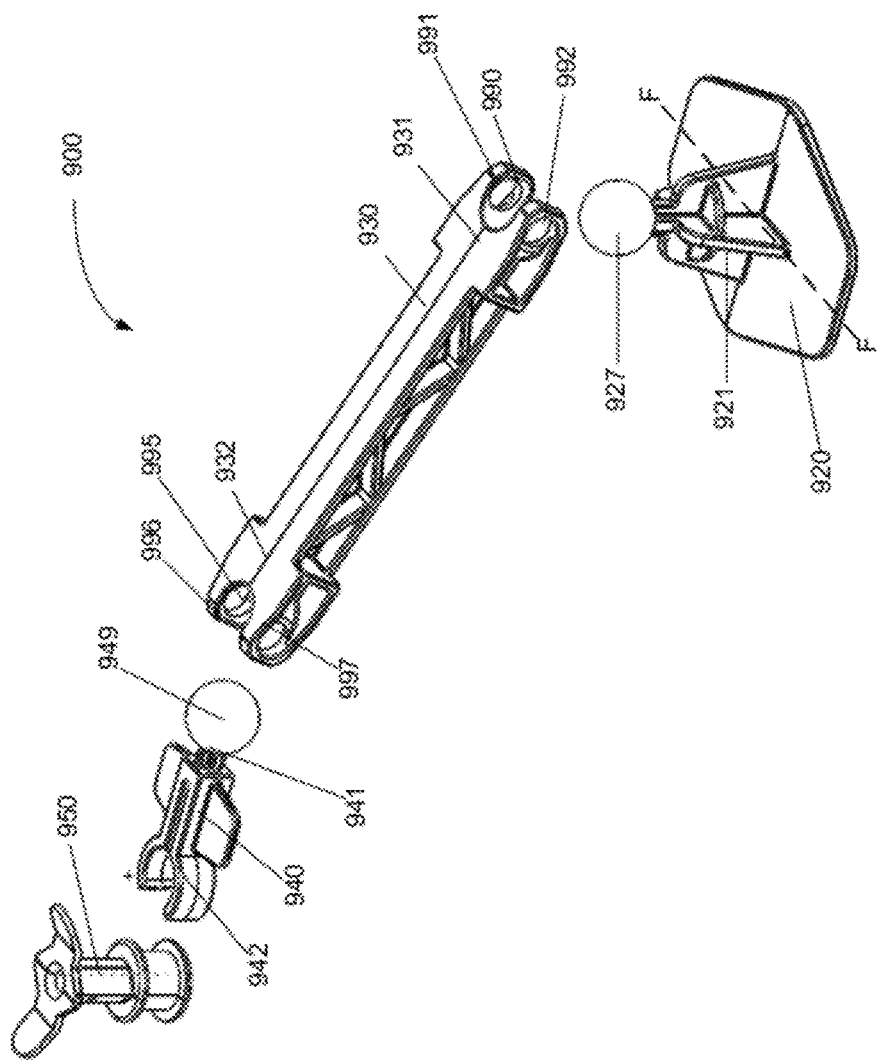
FIG. 29 is an exploded side perspective view of the stabilization device of FIG. 28.

In this embodiment, the base 920 includes a first protrusion 921 (see, e.g., FIG. 29). The first protrusion 921 includes a ball protrusion 927 that can be used to pivotally couple the support member 930 thereto. More specifically, the ball protrusion 927 can couple a first socket member 990 of the support member 930 to the base 920. Similarly stated, the base 920 and the support member 930 couple to form a ball and socket style fitting. The first protrusion 921 can be disposed at any suitable position on the base 920, for example, the center of the base 920 or along a longitudinal axis F, as shown in FIG. 32.

The support member 930 includes a first end portion 931, and a second end portion 932. The first end portion 931 includes or is coupled to the first socket member 990. The first socket member 990 includes a first arm 991 and a second arm 992. The ball protrusion 927 can be inserted (i.e., pushed) through an opening defined by the first socket protrusion 990 such that the first arm 991 and the second arm 992 of the first socket protrusion 990 flex or spread apart sufficiently to accept the first ball member 927 therein. Once fully inserted, the first socket protrusion 990 provides a pivotal coupling of the support member 930 to the base 920 such that the support member 930 can pivot and/or rotate relative to the base 920. While the first socket protrusion 990 includes a first arm 991 and a second arm 992, in other embodiments, the first socket protrusion 990 can include more arms, for example, the first socket protrusion 990 can include three arms extending in a triangular shape and defining the socket therein. Alternatively, the first socket protrusion 990 can include multiple arms that are not uniform, thereby coupling to the base 920 in a particular configuration and thus, tailoring the range of motion in a desired fashion.

Figure 28:
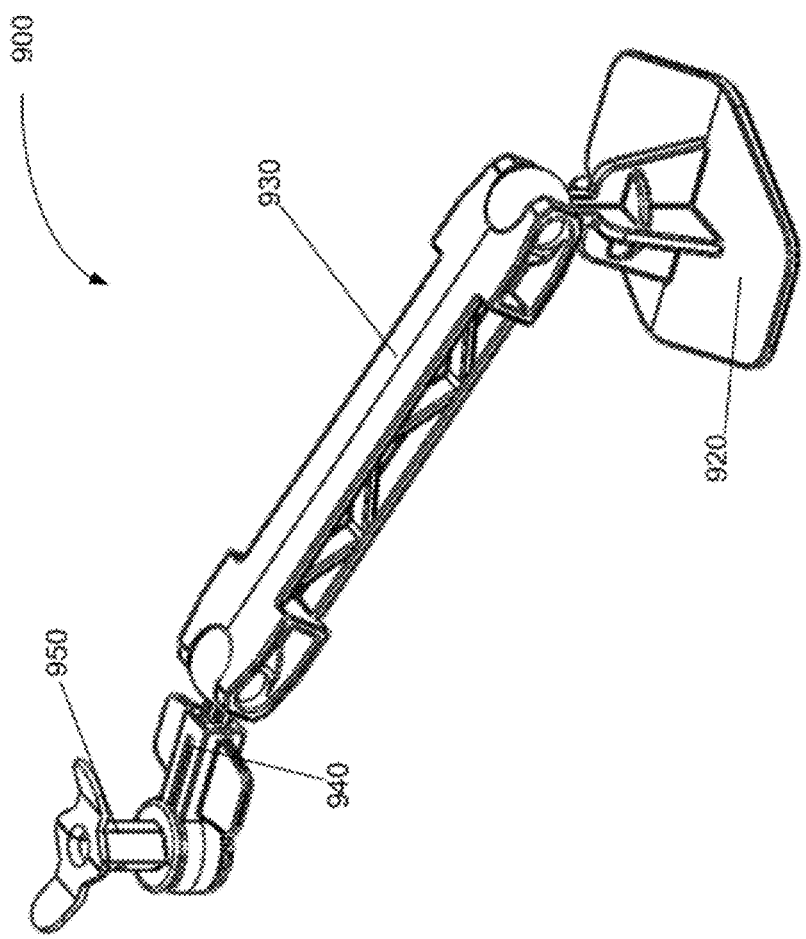
FIG. 28 is a side perspective view of a stabilization device, according to another embodiment.

When the first socket member 990 is coupled to the ball protrusion 927, the support member 930 extends from the base 920 at an angle transverse to the longitudinal axis F defined by the base 920, as shown, for example, in FIG. 28. Thus, the first end portion 931 can be disposed adjacent the base 920 and the second end portion 932 can extend at a desired angle relative to the base 920. The arrangement of the ball and socket coupling allows the angle formed between the support member 930 and the base 920 to be adjustable (i.e., not fixed) and, as such, can be disposed at different positions through a range of positions.

The support member 930 includes a set of stiffening ribs 998, as shown, for example, in FIG. 30. The stiffening ribs 998 make the support member 920 substantially rigid such that the movement of the second portion 932 is a result of the first socket member 990 moving around the surface of the ball protrusion 927. Although shown in FIG. 30 as substantially square in cross section, the support member 930 can be any suitable shape, for example, in some embodiments the support member 930 can be semi-cylindrical, rectangular, pentagonal, etc, and can include the stiffening ribs 998 disposed therein.

The second end portion 932 of the support member 930 includes a second socket member 995 that can be used to pivotally couple the support member 930 to a first end portion 941 of the clamping member 940. The first end portion 941 of the clamping member 940 includes a ball protrusion 949 the can extend axially from the first end portion 941 and can receive the second socket member 995 of the support member 930 (see, e.g., FIG. 29). The second socket protrusion 995 includes a first arm 996 and a second arm 997 that can be configured similar to or the same as the first arm 991 and the second arm 992 of the first socket member 990. The use of the ball and socket coupling allows the angle created between the support member 930 and the clamping member 940 to be adjustable (i.e., not fixed) and, as such, can be disposed at different positions through a range of positions.

The first socket protrusion 990 and the second socket protrusion 995 can be any suitable configuration and, in some embodiments, can be dissimilar. For example, the first socket protrusion 990 can be of a larger size and/or have a different configuration than the second socket protrusion 995. In some embodiments, the ball and socket joint can be replaced by a different coupling method, for example, a universal joint and/or the like.

As shown in FIG. 31, the clamping member 940 includes the first end 941, a second end 942, and a pair of wings 947. While shown as extending axially from the first end 941, in some embodiments, the ball protrusion 949 of the clamping member 940 can be disposed at any suitable position on the clamping member 940. For example, the ball protrusion 949 could be disposed at the middle of the clamping member 940 and can extend in a substantially downward direction. The clamping member 940 otherwise functions and is configured similarly to the clamping holder member 340 described above in connection with the stabilization device 300, and as such, is not further described here. Similarly, the holder member 950, shown in FIGS. 28 and 29, functions and is configured similarly to the holder member 350 described above in connection with the stabilization device 300, and as such, is not described here in depth.

The stabilization device 900 can be used to support or stabilize the position of the interventional tool (not shown in FIGS. 28-32) as described for previous embodiments. With the base 920 of the stabilization device 900 coupled to the skin of the patient, the stabilization device 900 can move with the patient though any potential motion (i.e., breathing or relaxation of muscles). This arrangement allows the interventional tool to maintain the desired angle and position relative to the patient, while not being actively moved by a clinician (e.g. physician, surgeon). Multiple stabilization devices 900 can be used simultaneously in close proximity, allowing for the use of two or more interventional devices during an interventional procedure as previously described.

Figure 33:
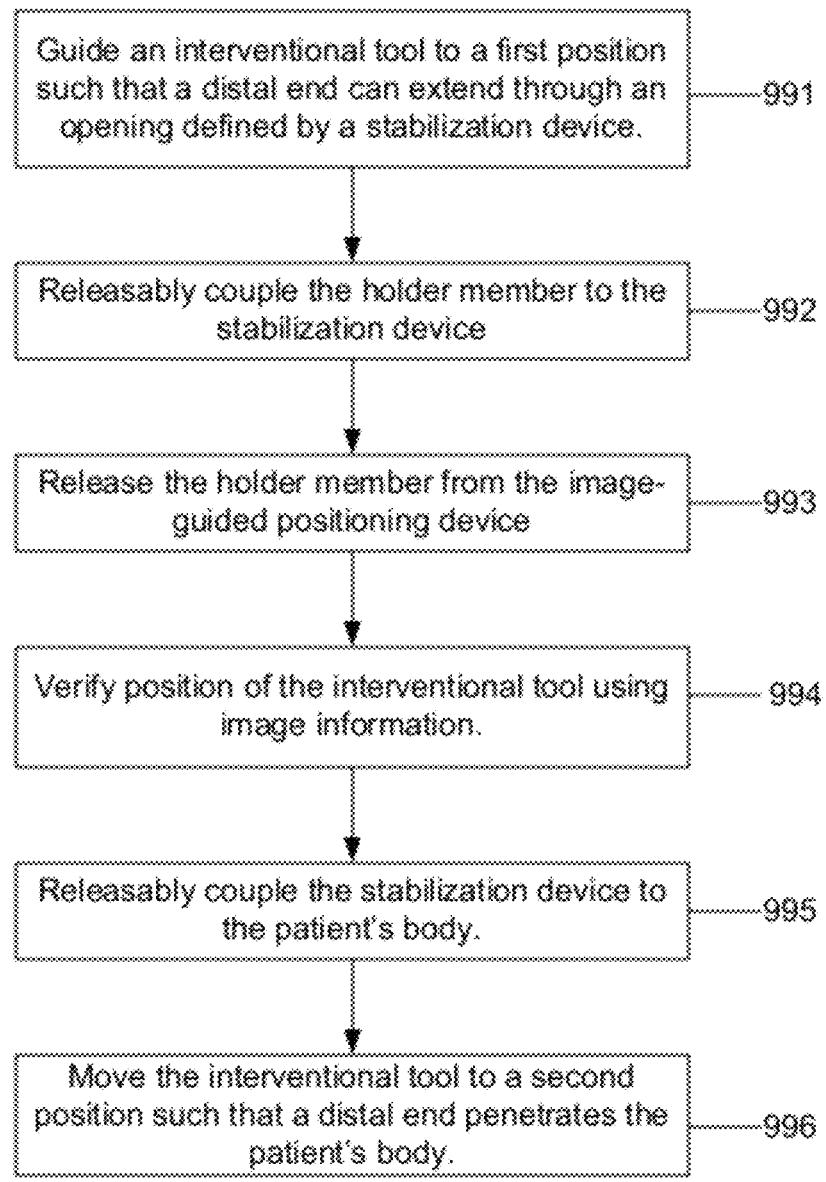
FIG. 33 is a flow chart illustrating a method of stabilizing an interventional tool during an interventional procedure, according to an embodiment.

FIG. 33 is a flowchart illustrating a method for stabilizing an interventional tool (e.g., a needle) during an interventional procedure using a stabilization device described herein. The example method described can be used, for example, during treatment of a tumor within a patient. The method includes guiding an interventional tool at a predetermined angle relative to a patient's body to a first position relative to the patient's body such that a distal end of the interventional tool extends through an opening defined by a holder member at 991. For example, during the guiding, the holder member can be coupled to a tool guide of an IGPD. The holder member can be releasably coupled to the stabilization device at 992. For example, as described herein with respect to stabilization device 200, the clamping member 240 of the stabilization device 200 can be releasably coupled to the holder member 250 as described in detail above. At 993, the holder member can be released from the tool guide of the IGPD. For example, in some embodiments, after the holder member has been coupled to the stabilization device it can be released from the tool guide. In some embodiments, the holder member can be released from the tool guide prior to being coupled to the stabilization device.

The position of the interventional tool can be verified using image information of the patient's body and the interventional tool, at 994. At 995, the stabilization device can be releasably coupled to the skin of the patient using any suitable method described herein. For example, the base may be coupled to the patient with an adhesive or using a suction force. At 996, the clinician can move the interventional tool to a second position such that a distal end of the interventional tool penetrates the skin of the patient and is disposed at a second position. The described method can be used for a stabilizing a second interventional tool that can be required in some interventional procedures.

CONCLUSION

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different from the embodiments shown, while still providing the functions as described herein.

What is claimed is:

1. An apparatus, comprising:
a base configured to be releasably coupled to a patient's skin, the base defining a longitudinal axis;
a support portion extending from the base at an angle transverse to the longitudinal axis defined by the base, the support portion having a first end portion and a second end portion, the first end portion disposed adjacent the base;
a holder portion extending from the second end portion of the support portion in a first direction, the holder portion defining an opening configured to receive an interventional tool therethrough;
a first rib member extending from the support portion in a second direction opposite the first direction; and
a second rib member extending from the support portion in the second direction, the first rib member and the second rib member each being pivotally movable relative to the support portion from a first configuration in which the first rib member and the second rib member are substantially parallel to each other and the opening defined by the holder portion has a first size, and a second configuration in which the first rib member and the second rib member are each pivoted relative to the support portion and toward each other and the opening defined by the holder portion has a second size greater than the first size.

2. The apparatus of claim 1, wherein when the first rib member and the second rib member are in the first configuration, the holder portion is configured to releasably maintain the interventional tool within the opening.

3. The apparatus of claim 1, wherein the holder portion includes a first holder arm and a second holder arm that collectively define the opening.

4. The apparatus of claim 1, further comprising:
an adjustment mechanism coupled to the holder portion, the adjustment mechanism configured to be moved between a first configuration in which an opening defined by the adjustment mechanism has a first size and a second configuration in which the opening of the adjustment mechanism has a second size different than the first size.

5. The apparatus of claim 1, wherein the first size of the opening is a first diameter of the opening, the second size of the opening is a second diameter of the opening, the holder portion includes an adjustment portion configured to selectively adjust the diameter of the opening defined by the holder portion between a plurality of diameters, the plurality of diameters including the first diameter and the second diameter.

6. The apparatus of claim 1, wherein the base is configured to be adhesively coupled to the patient's skin.

7. The apparatus of claim 1, wherein the base is configured to be coupled to the patient's skin using a suction force.

8. The apparatus of claim 1, wherein the interventional tool is a needle.

9. An apparatus, comprising:
a base configured to be releasably coupled to a patient's skin;
an elongate support member coupled to the base, the elongate support member having a first end portion and a second end portion, the first end portion being coupled to the base;
a holder member releasably couplable to the second end portion of the elongate support member, the tool guide configured to guide an interventional tool during an image guided interventional procedure at a predetermined angle relative to the patient's body,
the holder member configured to be coupled to a tool guide of an image guided positioning device during an image guided interventional procedure, the tool guide configured to guide an interventional tool during an image guided interventional procedure at a predetermined angle relative to the patient's body,
the holder member configured to be movable from a first position in which a first coupling portion of the holder member is coupled to the tool guide and the holder member is not coupled to the second end portion of the elongate support member, and a second position in which a second coupling portion of the holder member is coupled to a clamp device coupled to the second end portion of the elongate support member and configured to stabilize the interventional tool at the predetermined angle relative to the patient's body.

10. The apparatus of claim 9, wherein the clamp device is pivotally coupled to the second end portion of the elongate support member, the holder member being releasably couplable to the clamp device, the clamp device and the holder member collectively being pivotally movable relative to the support member when the holder member is coupled to the clamp device.

11. The apparatus of claim 9, wherein the first end portion of the support member is pivotally coupled to the base.

12. The apparatus of claim 9, wherein the base is configured to be adhesively coupled to the patient's skin.

13. The apparatus of claim 9, wherein the base is configured to be coupled to the patient's skin with a suction force.

14. The apparatus of claim 9, wherein the interventional tool is a needle.

15. An apparatus, comprising:
a base configured to be releasably coupled to a patient's skin;
an elongate support member coupled to the base, the elongate support member having a first end portion and a second end portion, the first end portion being coupled to the base;
a holder member releasably couplable to the second end portion of the elongate support member; and
an image-guided positioning device disposed adjacent the patient, the image-guided positioning device including a tool guide, the tool guide configured to guide an interventional tool during an image guided interventional procedure at a predetermined angle relative to the patient's body,
the holder member configured to be coupled to the tool guide of the image guided positioning device during an image guided interventional procedure,
the holder member configured to be movable from a first position in which the holder member is coupled to the tool guide and is not coupled to the second end portion of the elongate support member and a second position in which the holder member is coupled to a clamp device coupled to the second end portion of the elongate support member and configured to stabilize the interventional tool at the predetermined angle relative to the patient's body.

16. The apparatus of claim 15, wherein the base is configured to be adhesively coupled to the patient's skin.

17. The apparatus of claim 15, wherein the base is configured to be coupled to the patient's skin with a suction force.

18. The apparatus of claim 15,
wherein the clamp device is pivotally coupled to the second end portion of the elongate support member, the holder member being releasably couplable to the clamp device.

19. The apparatus of claim 15, wherein the image-guided positioning device is configured to verify a position of the interventional tool relative to the patient's body using image information of the patient's body and the interventional tool.

20. The apparatus of claim 9, wherein the tool guide is configured to guide an interventional tool during an image guided interventional procedure at a predetermined height relative to the patient's body.

21. The apparatus of claim 15, wherein the tool guide is configured to guide an interventional tool during an image guided interventional procedure at a predetermined height relative to the patient's body.

* * * * *

UNITED STATES PATENT AND TRADEMARK OFFICE
CERTIFICATE OF CORRECTION

PATENT NO.        : 8,613,748 B2           Page 1 of 1
APPLICATION NO.   : 13/435963
DATED             : December 24, 2013
INVENTOR(S)       : Gnanasekar Velusamy et al.

It is certified that error appears in the above-identified patent and that said Letters Patent is hereby corrected as shown below:

Title page, item (30) (Foreign Application Priority Data), replace with the following:

--Nov. 10, 2010 (IN)          3363/CHE/2010
  Aug. 19, 2011 (IN)          3363/CHE/2010--

Signed and Sealed this
Third Day of June, 2014

Michelle K. Lee
*Deputy Director of the United States Patent and Trademark Office*